US009007593B2

(12) United States Patent
Sailor et al.

(10) Patent No.: US 9,007,593 B2
(45) Date of Patent: Apr. 14, 2015

(54) TEMPERATURE RESPONSE SENSING AND CLASSIFICATION OF ANALYTES WITH POROUS OPTICAL FILMS

(75) Inventors: Michael J. Sailor, La Jolla, CA (US); Brian H King, Arlington, VA (US); Sadafumi Noda, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 76 days.

(21) Appl. No.: 13/811,147

(22) PCT Filed: Jul. 19, 2011

(86) PCT No.: PCT/US2011/044549
§ 371 (c)(1),
(2), (4) Date: Jan. 18, 2013

(87) PCT Pub. No.: WO2012/012437
PCT Pub. Date: Jan. 26, 2012

(65) Prior Publication Data
US 2013/0114082 A1    May 9, 2013

Related U.S. Application Data

(60) Provisional application No. 61/365,839, filed on Jul. 20, 2010, provisional application No. 61/368,745, filed on Jul. 29, 2010.

(51) Int. Cl.
*G01N 21/00* (2006.01)
*G01N 21/25* (2006.01)
*G01N 21/17* (2006.01)

(52) U.S. Cl.
CPC .............. *G01N 21/25* (2013.01); *G01N 21/171* (2013.01)

(58) Field of Classification Search
USPC ................. 356/445–448, 432–440, 301–402; 435/287.1–287.3; 436/101, 164–165, 436/518, 524, 527, 805
See application file for complete search history.

(56) References Cited

U.S. PATENT DOCUMENTS 5,120,131 A    6/1992  Lukosz
6,130,748 A   10/2000  Kruger et al.
(Continued)

FOREIGN PATENT DOCUMENTS

JP     06-273303     9/1994
WO   WO 03/067231   8/2003
(Continued)

OTHER PUBLICATIONS

Anson, M.L., "The Estimation of Pepsin, Trypsin, Papain, and Cathepsin with Hemoglobin", *The Journal of General Physiology*, 22(1), Sep. 20, 1938, pp. 79-89.
(Continued)

*Primary Examiner* — Hoa Pham
(74) *Attorney, Agent, or Firm* — Greer, Burns & Crain, Ltd.

(57) ABSTRACT

Methods and systems of the invention can determine the identity and quantity of analytes in a vapor. In preferred methods, a porous optical film is exposed to vapor which contains analyte. The porous optical film is heated and its optical response is monitored during heating. An optical response observed via heating can determine the identity and/or quantity of the analyte. In preferred embodiments, optical response during a thermal pulse is compared to a database of sensor responses that are characteristic of various analytes. Preferred methods are conducted a relatively low temperatures, for example below about 200° C. In preferred methods, a heating and cooling cycle produces a hysteresis curve in the optical response that is indicative of analytes. In preferred embodiments, a thermal reset pulse resets the porous optical film for later use and also provides an optical response that can be used for sensing.

23 Claims, 19 Drawing Sheets

(56) References Cited

U.S. PATENT DOCUMENTS

| | | | |
|---|---|---|---|
| 6,435,008 B2* | 8/2002 | Baklanov et al. | 73/38 |
| 6,989,897 B2* | 1/2006 | Chan et al. | 356/301 |
| 7,042,570 B2 | 5/2006 | Sailor et al. | |
| 8,206,780 B2* | 6/2012 | Li et al. | 427/162 |
| 8,274,643 B2* | 9/2012 | Sailor et al. | 356/38 |
| 8,778,690 B2* | 7/2014 | Sailor et al. | 436/101 |
| 2002/0192680 A1 | 12/2002 | Chan et al. | |
| 2003/0146109 A1 | 8/2003 | Sailor et al. | |
| 2005/0266045 A1 | 12/2005 | Canham et al. | |
| 2008/0219615 A1 | 9/2008 | Cunningham | |
| 2008/0252890 A1 | 10/2008 | Noda et al. | |
| 2009/0179171 A1 | 7/2009 | Sailor et al. | |
| 2010/0008619 A1 | 1/2010 | Sailor et al. | |

FOREIGN PATENT DOCUMENTS

| | | |
|---|---|---|
| WO | WO 2005/062865 | 7/2005 |
| WO | WO 2006/044957 | 4/2006 |
| WO | WO 2008/086448 | 7/2008 |

OTHER PUBLICATIONS

Buriak, J. M., et. al. "Organometallic Chemistry on Silicon and Germanium Surfaces." *Chem. Rev.* 102(5): 1272-1308, 2002.

Cazzanelli, M. et. al., "Temperature dependence of the photoluminescence of all-porous-silicon optical microcavities", *Journal of Applied Physics*, vol. 85, No. 3, Feb. 1, 1999, pp. 1760-1764.

Canham, L.T., et. al. "Derivatized Porous Silicon Mirrors: Implantable Optical Components with Slow Resorbability", *phsy. Stat. sol.* (a), 182, 521, (2000), pp. 521-525.

Das, J.O., et. al., "A hygrometer comprising a porous silicon humidity sensor with phase-detection electronics.", *IEEE Sensors Journal*, 3(4): 414-420, 2003.

Foucaran, A., et. al., "Porous silicon layer coupled with thermoelectric cooler: a humidity sensor.", *Sensors and Actuators*, 79(3): 189-193, 2000.

Gao, Jun, et. al. "Porous-silicon vaper sensor based on laser interferometry", *Applied Physics Letters*, vol. 77, No. 6, Aug. 7, 2000, pp. 901-903.

Ichimura, Kunihiro, et. al., "Light-Driven Motion of Liquids on a Photoresponsie Surface", *Science*, (2000), 288, 1624.

Kang. U.S., et. al., "A high-speed capacitive humidity sensor with on-chip thermal reset.", *IEEE Transactions on Electron Devices*, 47(4): 702-710, 2000.

King, Brian, et. al., "Optical-Fiber-Mounted Porous Silicon Photonic Crystals for Sensing Organic Vapor Breakthrough in Activated Carbon", *Adv. Mater.*, 2007, 19, 4530-4534.

Lee, Andrew P., et. al. "Temperature modulation in semiconductor gas sensing", *Sensors and Actuators B*, (1999) 35-42.

Letant, S., et. al., Molecular identification by time resolved interferometry in a porous silicon film, *Adv. Mat.*, 13(5): 335-338, 2001.

Lin, Victor S.-Y., et. al., "A Porous Silicon-Based Optical Interferometric Biosensor", *Science*, vol. 278, Oct. 31, 1997, pp. 840-843.

Link, Jamie R., et. al., "Smart dust: Self-assembling, self-orienting photonic crystals of porous Si", *PNAS*, Sep. 16, 2003, vol. 100, No. 19, 10607-10610; published online before print, Aug. 28, 2003, doi:10.1073/pnas.1233824100.

Motohashi, A., et. al., "Identification of water molecules in low humidity and possibility of quantitative gas analysis using porous silicon gas sensor", *Japanese Journal of Applied Physics Part 1—Regular Papers Short Notes & Review Papers*, 35(8): 4253-4256, 1996.

Nakata, S., et. al., "Non-linear dynamic responses of a semiconductor gas sensor—Competition effect on the sensor responses to gaseous mixtures", *Thin Solid Films*, vol. 391, No. 2, Jul. 16, 2001, pp. 293-298.

Oda, R. P., et. al. "Infrared-Mediated Thermocycling for Ultrafast Polymerase Chain Reaction Amplification of DNA", *Anal. Chem.*, 1998, 70, pp. 4361-4368.

Pacholski, Claudia, et. al., "Reflective Interferometric Fourier Transform Spectroscopy: A Self-Compensating Lable-Free Immunosensor Using Double-Layers of Porous $SiO_2$", *J. Am. Chem. Soc.*, 2006, 128, 4250-4252.

Park, Jae,-Sook, et. al., "Enhancement of Sensitivity in Interferometric Biosensing by Using a New Biolinker and Prebinding Antibody", *J. Microbiol. Biotechnol.*, (2006) 16(12), 1968-1976.

Rittersma, Z., et. al., "A novel surface-micromachined capacitive porous silicon humidity sensor." *Sensors and Actuators B-Chemical*, 68(1-3): 210-217, 2000.

Rittersma, Z., et. al., "A monitoring instrument with capacitive porous silicon humidity sensors", *Smart Materials & Structures*, 9(3): 351-356, 2000.

Ruminski, Anne M., et. al., "Humidity-Compensating Sensor for Volatile Organic Compounds Using Stacked Porous Silicon Photonic Crystals", *Adv. Funct. Mater.*, (2008), 18, 3418-3426.

Ruminski, Anne M., et. al., "Internally Referenced Remote Sensors for HF and $Cl_2$ Using Reactive Porous Silicon Photonic Crystals", *Adv. Funct. Mater.*, (2011), 21, 1511-1525.

Salem, M.S., et. al., "Sensitivity of porous silicon rugate filters for chemical vapor detection.", *Journal of Applied Physics*, 103(8), 2008, pp. 083516-1-083516-7.

Salem, M.S., et. al., "Electrochemical stabilization of porous silicon multilayers for sensing various chemical compounds.", *Journal of Applied Physics*, 100(8), 2006 pp. 083520-083520-7.

Salonen, J., et. al., Studies of Thermally-Carbonized Porous Silicon Surfaces., *physica status solidi* (a), 182(1): 123-126, 2000.

Salonen, J. et. al., "Sub-ppm trace moisture detection with a simple thermally carbonized porous silicon sensor." *Sensors and Actuators*, 114: 423-425, 2006.

Tay, Chia Meng, et. al. "Humidity sensing using plastic optical fibers", *Microw. Opt. Technol. Lett.*, 43: 387-390, Dec. 5, 2004.

Tsamis, C. et. al., "Thermal properties of suspended porous silicon micro-hotplates for sensor applications." *Sensors and Actuators B-Chemical*, 95(13): 78-82, 2003.

Thoenissen, M., et. al. "1.4 Multilayer structures of porous silicon", *Properties of Porous Silicon*, pp. 30-58, May 1997.

Wang, Anbo, et. al. "Fiber-optic temperature sensors based on differential spectral transmittance/reflectivity and multiplexed sensing systems", *Applied Optics*, vol. 34, No. 13, May 1, 1995, pp. 2295-2300.

Warneke, Brett, et. al. "Smart Dust: Communicating with a Cubic-Millimeter Computer", *Computer*, vol. 34, Issue 1, Jan. 2001, pp. 44-51.

Xiao, Gao Zhi, et. al., "Monitoring changes in the refractive index of gases by means of a fiber optic Fabry-Perot interferometer sensor", *Sensors and Actuators A*, 118 (2005) 177-182.

Zangooie, S., et. al., "Protein adsorption in thermally oxidized porous silicon layers", *Thin Solid Films*, 313-314, (1998), 825-830.

Zhou, Y. et. al., "The Effect of Thermal Processing on Multilayer Porous Silicon Microcavity", *phys. stat. so.* (a), 182, 319-324 (2000).

* cited by examiner

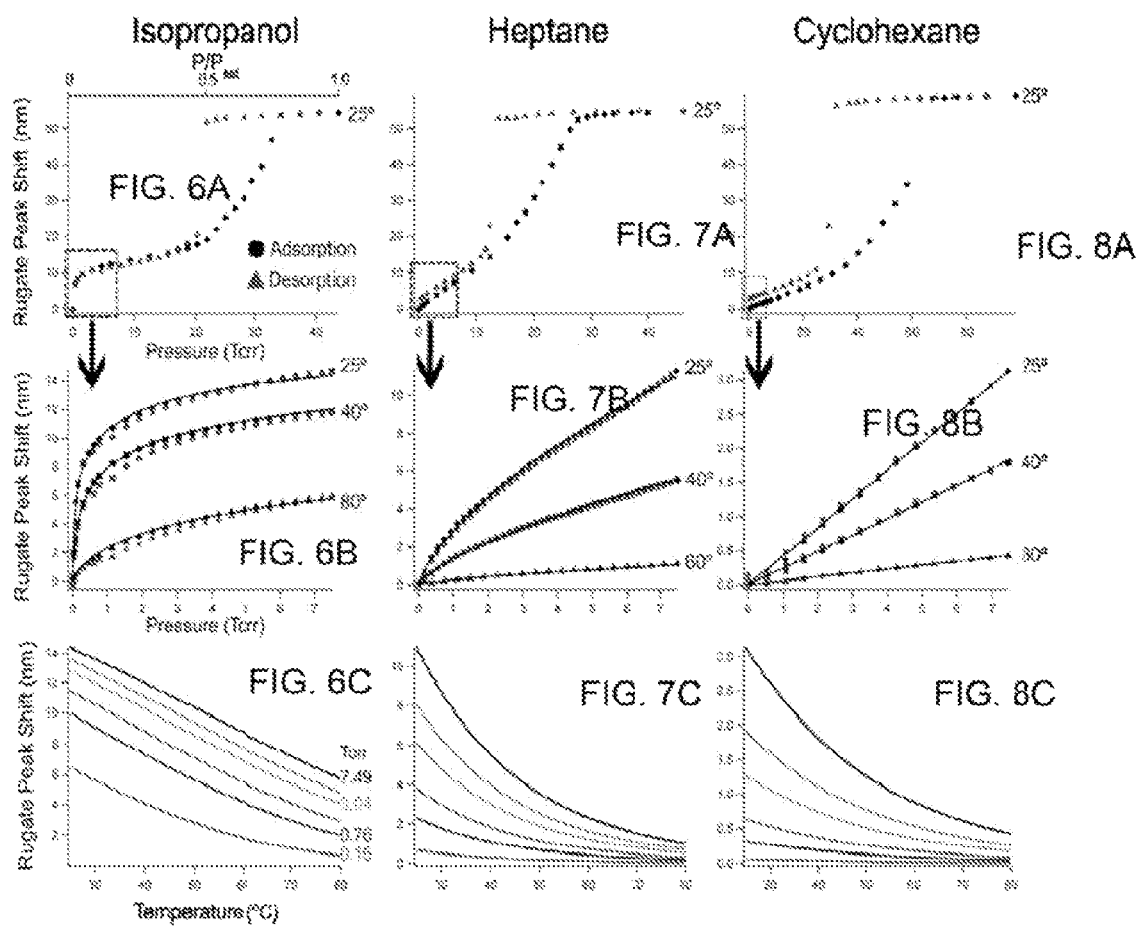

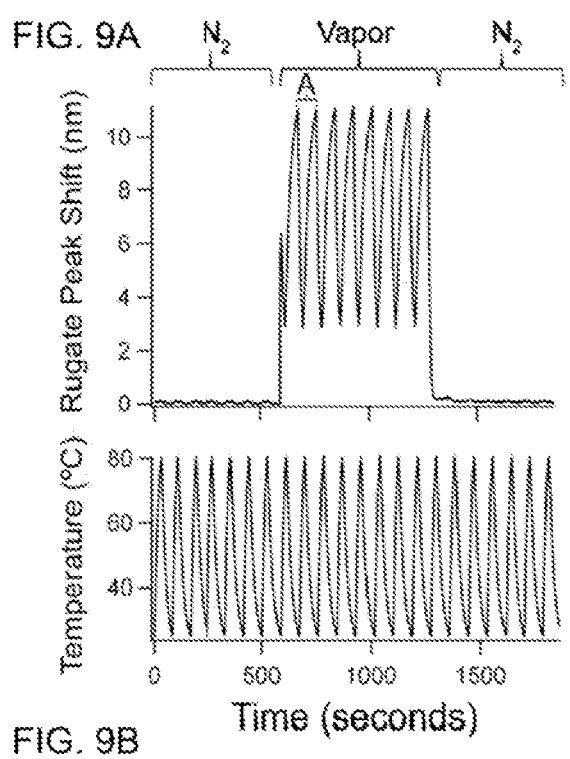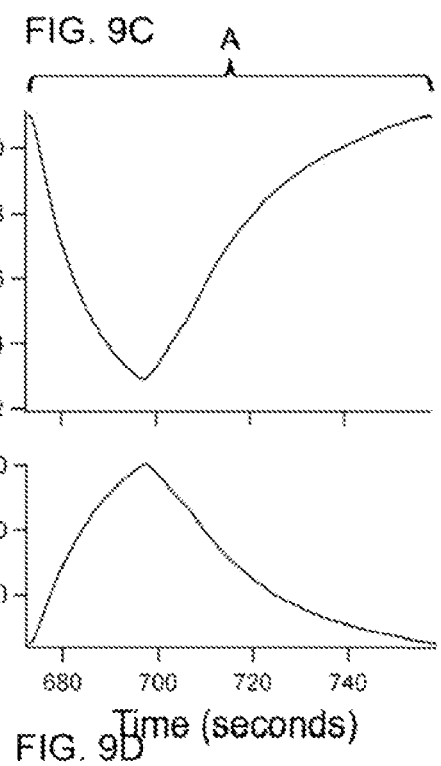

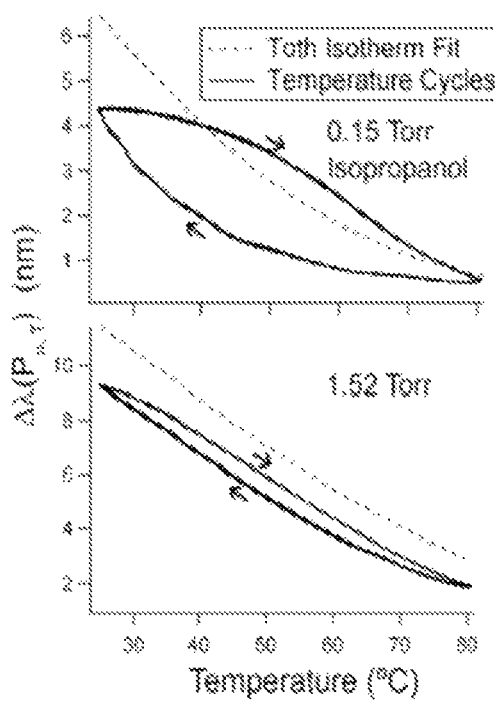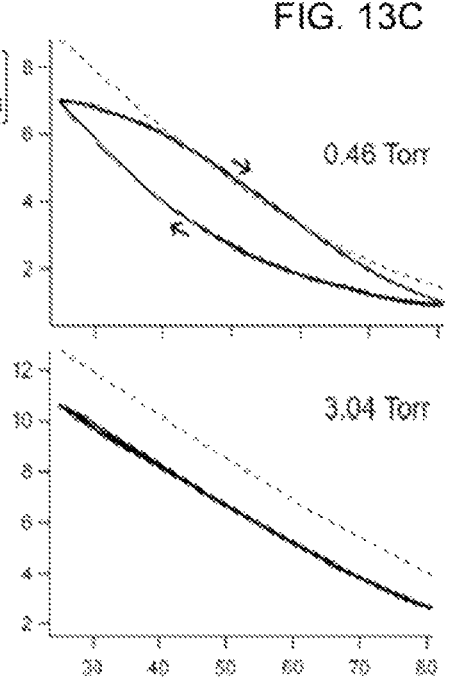
FIG. 13A  FIG. 13B  FIG. 13C  FIG. 13D

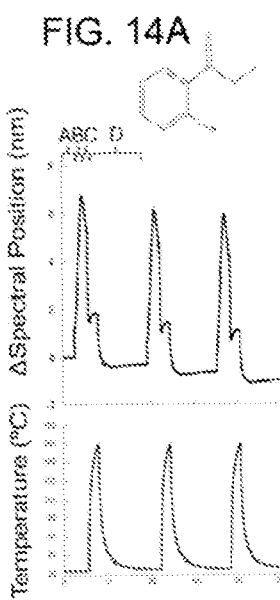
FIG. 14A
FIG. 14B
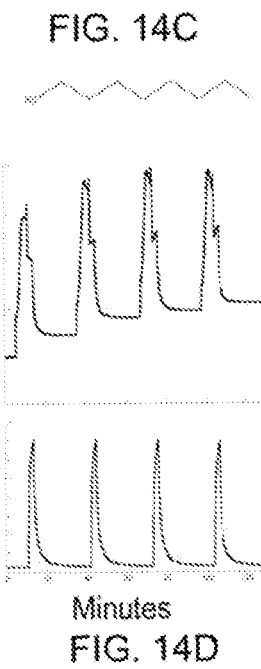
FIG. 14C
FIG. 14D
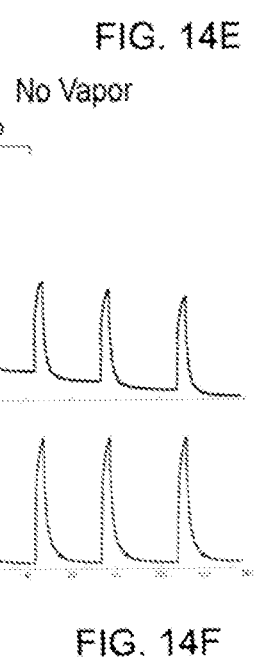
FIG. 14E
FIG. 14F

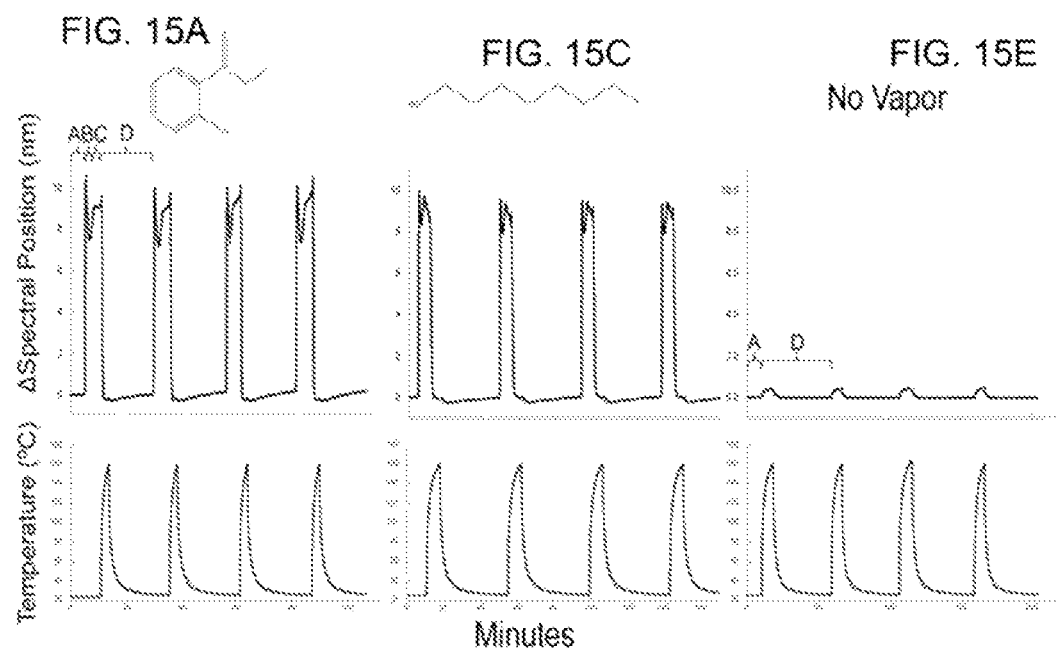

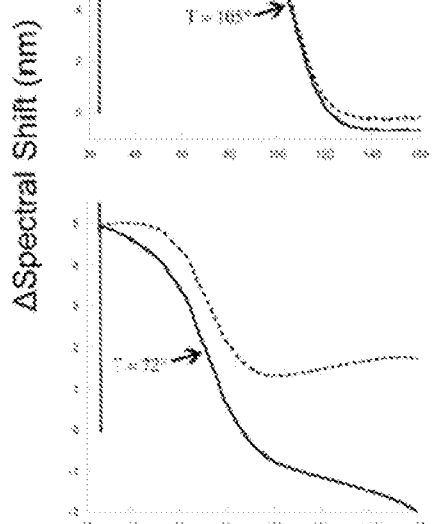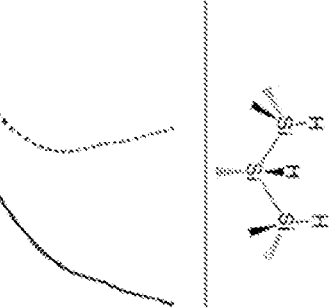
FIG. 16A  FIG. 16B  FIG. 16C  FIG. 16D

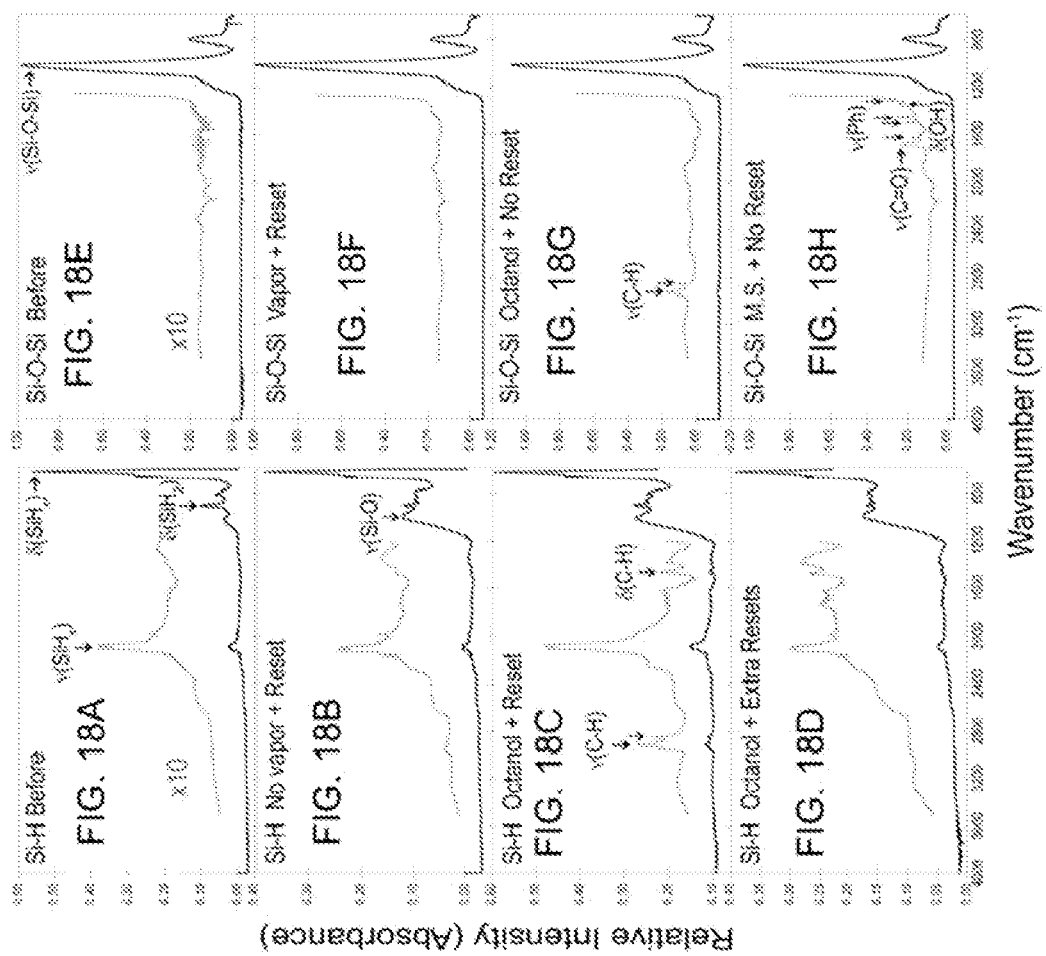

US 9,007,593 B2

TEMPERATURE RESPONSE SENSING AND CLASSIFICATION OF ANALYTES WITH POROUS OPTICAL FILMS

PRIORITY CLAIM AND REFERENCE TO RELATED APPLICATION

This application claims priority under 35 U.S.C. §119 and all other applicable statutes and treaties from U.S. provisional application Ser. No. 61/365,839, which was filed on Jul. 20, 2010 and from U.S. provisional application Ser. No. 61/365,745, which was filed on Jul. 27, 2011.

STATEMENT OF GOVERNMENT INTEREST

This invention was made with government support under Contract No. DMR-0806859 awarded by the National Science Foundation. The government has certain rights in the invention.

FIELD OF THE INVENTION

Fields of the invention include chemical sensing, gas analysis, and multi-component analysis.

BACKGROUND OF THE INVENTION

Optical films such as Fabry Perot layers and photonic crystals have recently attracted attention as sensitive detectors of chemical or biological compounds. Prominent features of sensing with porous materials such as porous silicon, porous silicon oxide, or porous alumina are their small size, their stability, and their high sensitivity. Although the interaction between a porous optical film and an analyte does not involve a chemical reaction, it is able to detect the analyte optically. The detection is derived from changes to the optical band gap of the porous optical film, which is influenced by the difference of the refractive index between porous substrate and atmosphere. The optical characteristics of a porous optical film can be controlled during fabrication by adjusting the pore size and pore shape. Example applications of porous optical films include as a chemical sensor (WO 2006/044957), as a vapor sensor (US2008/252890; M. S. Salem et al. J. Appl. Phys. 2006, 100, 083520; B. H. King et al. Adv. Mater. 2007, 19, 4530-4534), a biosensor (US 2008/219615) and an acoustic sensor (WO 2008/086448). The films provide large surface areas, various surface chemistries and controllable optical and morphological properties including pore size, porosity, and refractive index allow the porous material to be tailored to specific sensing applications. The films can be formed to create various optical structures including Bragg mirrors, Fabry-Perot film, microcavities, and Rugate filters. Sinusoidal variations in the porous silicon refractive index with depth results in Rugate filters that provide a reflection stop band at a wavelength determined by the amplitude and period of the refractive index modulation. Infiltration of chemical vapors into the porous film shifts this spectral peak by increasing the refractive index of the porous layer thereby enabling transduction of ambient vapors by monitoring the magnitude and time evolution of the reflected stop band or Rugate peak wavelength. Films can be formed in various semiconductors and insulators, however, porous silicon is especially favored as it is inexpensive, readily oxidized and also provides biocompatibility. Most sensing has been conducted at ambient temperatures.

Susumu, et al, U.S. Published Application No. US2008/0252890 discloses a photonic sensor that includes a heating element. In Susuma, the heating element is used to refresh the sensor. It is also used as one of a number of methods to periodically modulate intensity or wavelength of the electromagnetic wave emitted from the sensor to permit detection of only the modulated electromagnetic wave, which helps distinguish a desired signal intensity peak from noise. The modulation of the signal wavelength by heat or other techniques in Susuma permits an analyzer to select only the modulated electromagnetic wave from others detected at the detector to discriminate the signal from electromagnetic wave noises at the detector. The modulation permits selection of the signal. Upon selection of the correct signal, the electromagnetic detector in Susumu utilizes a simple intensity measurement to determine the density of a substance introduced to the sensor. The intensity of the signal is compared with a reference intensity and the attenuation in the signal wavelength as compared to reference wavelength is used to determine the density.

Others have used temperature modulation during conductivity sensing as reported by Lee et al in "Temperature Modulation in Semiconductor Gas Sensing," Sensors and Actuators B-Chemical, 60 (1999). The Lee article discusses temperature dependence of sensor conductance, along with transient and cyclic modulation techniques for improving sensitivity and selectivity of conductivity sensors in the analysis of single gases and multi-component gas mixtures. An illustrative example of these techniques is described by Nakata et al, in "Non-Linear Dynamic Responses of a Semiconductor Gas Sensor—Competition Effect on the Sensor Responses to Gaseous Mixtures," Thin Solid Films, Volume 391, Issue 2, 16, pp 293-298 (July 2001). Nakata applied sinusoidal temperature cycles to semiconductor conductivity sensors and assessed the characteristic conductance-temperature profiles of light hydrocarbons. Others have also used programmed temperature profiles on arrays of metal oxide films to separate analyte behavior based on conductivity measurement. The conductivity changes are inspired in such approaches by high temperatures ranging from 200-600° C.

SUMMARY OF THE INVENTION

Methods and systems of the invention can determine the identify and quantify of analytes in a vapor. In preferred methods, a porous optical film is exposed to vapor which contains analyte. The porous optical film is heated and its optical response is monitored during heating. An optical response observed via heating can determine the identity and/or quantity of the analyte. In preferred embodiments, optical response during a thermal pulse is compared to a database of sensor responses that are characteristic of various analytes. Preferred methods are conducted a relatively low temperatures, for example below about 200° C. In preferred methods, a heating and cooling cycle produces a hysteresis curve in the optical response that is indicative of analytes. In preferred embodiments, a thermal reset pulse resets the porous optical film for later use and also provides an optical response that can be used for sensing.

DESCRIPTION OF THE DRAWINGS

FIGS. 6A-8C are experimental results of isothermal peak shifts of a sensor for Isopropanol, Heptane, and Cyclohexane;

FIGS. 9A-9D illustrate experimental data obtained for continuous cycling during simultaneous spectral acquisition that demonstrate rapid thermal response and reset;

FIGS. 13A-13D illustrate experimental data showing different spectral response plots at different pressures of isopropanol;

FIGS. 14A-15F show experimental data relating to optical events for a thermal result pulse for freshly prepared samples in FIGS. 14A-14F and for oxidized samples in FIGS. 15A-15F for a number of analytes;.

FIGS. 16A-16D show one cycle of thermal refresh of spectral shift versus temperature for fresh and oxide sensor films for two analytes, illustrating that the second derivative of the shift provides analyte identification; FIGS. 18A-18H show experimental data illustrating the beneficial effect of thermal pulse reset and the accumulated additive responses in the case of no reset.

DETAILED DESCRIPTION OF THE PREFERRED EMBODIMENTS

Figure 1A:
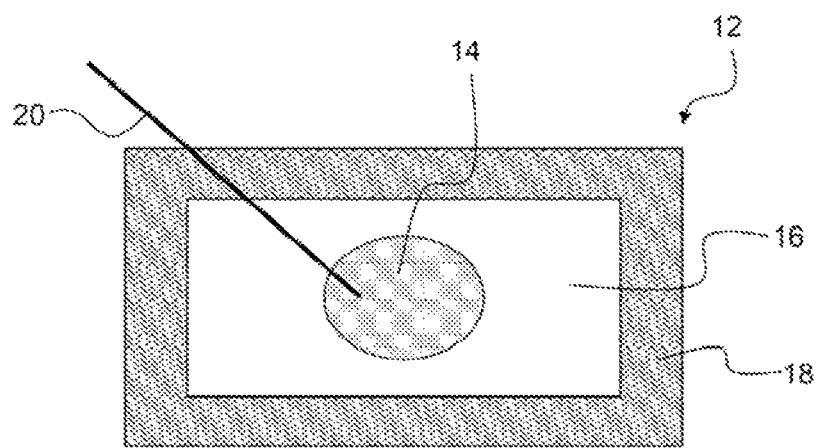
FIG. 1A illustrates a preferred sensor of the invention.

Methods and systems of the invention leverage the optical characteristics of porous optical films during heating cycles, and in additional embodiments during cooling cycles. The inventors have deter mined that optical responses obtained during thermal cycling periods, including thermal cycling at relatively low temperatures below about 200° C. in one example, produce information in the optical response that is unique to particular analyst. Heating of a sensing film, e.g., through heating element near the sensor element, or in contact with the sensing film is conducted to locally heat the film, preferably without substantially heating a vapor stream being examined. In preferred embodiments, hysteresis curves identifying particular analytes are determined and stored as a database that can be used during sensing to determine analytes in a vapor stream. In preferred embodiments a reset thermal pulse resets the sensor for additional use, but also provides a period of thermal reset where the optical response of the porous optical film is monitored for sensing purposes to determine the identity and/or quantity of analyte in the vapor stream.

The inventors have identified molecule unique thermal induced optical responses from porous optical films that permit determination of the identity of analyte molecules introduced to the porous optical films. Experiments conducted by the inventors have shown that methods of the invention are surprisingly effective even if the interaction between the analyte and a porous optical film is strong. In preferred methods, the sensor element is reset effectively by heating that also provides a characteristic optical response.

A preferred sensor used in methods and systems of the invention includes bulk semiconductor or insulator material with a porous sensing region therein. In preferred embodiments, the semiconductor or insulator material is highly doped silicon. The bulk material, such as a substrate, is heated by a heater, such as a resistive heater or lamp, and a temperature sensor monitors temperature of the porous sensing material. A control system controls the heating and monitoring during a sensing operation. A method for sensing uses the temperature response of a porous optical film to sense vapor molecules and acquire classification information about the molecules. The information can in some cases be time-correlated.

A database of previously obtained responses can be used by a controller to determine the identity of an analyte. The optical response also includes information that can be used determine the quantify of analyte. In preferred embodiments, the response is monitored over a sensing time period that includes at least a portion of both a heating and cooling cycle. The stored previously obtained responses include hysteresis curves that are unique to specific molecule and permit identification. The database can also include information about spectral shifts in the optical bandgap during the heating and cooling periods and/or during a thermal pulse reset heating period.

Preferred sensors and methods of the invention have some favorable qualities. The sensing material is stable to temperatures that are necessary to rest the sensor region and desorb molecules from the sensor region, e.g., greater than 160° C., in that it retains its optical properties and sensing capability. This allows the material to undergo thermal cycling. Most low power point sensor technologies cannot withstand such thermal treatments. The sensor is stable after being cycled to such reset temperatures multiple times. The sensor does not require a constant elevated temperature for operation, unlike many metal oxide sensors, thus saving power requirements, and can operate in a relatively low temperature range below about 200° C., which is advantageous for analyte molecules with high vapor pressures (which includes many VOCs, and volatile organic compounds, for example) or desorb from the sensing surface at higher temperatures.

The optical sensor does not require a "burn in" or heating/conditioning period, unlike metal oxide sensors. Heavy analytes are thermally expunged by the sensor, unlike those sensors lacking such a reset capability. In a preferred operational sequence, the sensor is cycled up and down in temperature, and analyte identification information is collected by during the cycling, which eliminates the need to purge the sensor with vapor-free air or nitrogen between scans.

Preferred methods of sensing and identifying a vapor analyte with a porous optical film detect the shift in the spectral position of its optical band gap. In preferred methods, direct recovery of the response of the porous optical film is provided by heating the film to 60° C. or more for reusable sensing. By desorbing analytes that slowly diffuse out of the sensor's porous matrix, the thermal pulse quickly resets the sensor response and shortens the time required between sensing events.

According to another aspect of the invention, identification of analytes is provided by comparing the sensor response in a period of time surrounding the thermal pulse to a database of sensor responses to various analytes. Thus, the information collected during the application of the thermal pulse is used to determine the properties of the sensed analyte. Depending on the sensor configuration, this information can be used to identify class-specific (hydrophobicity, high or low vapor pressure, etc.) or analyte-specific characteristics and/or analyte concentration. Periodic, cycled applications of the thermal pulse allow for continuous sensing events, each comprised of a thermally induced cycle of analyte desorption and subsequent cooling. The information collected from the sensor response includes equilibrium information, such as changes in the wavelength position of the optical film's spectral peak(s), and kinetic information, such as the rate of change, shape, and functional form of the sensor response.

Preferred embodiments of the invention will now be discussed with respect to experiments that have been conducted and with respect to the drawings. The drawings may include schematic representations, which will be understood by artisans in view of the general knowledge in the art and the description that follows. Features may be exaggerated in the drawings for emphasis, and features may not be to scale. Artisans will also understand general methods and systems of the invention from the specific experiments that were conducted.

Figure 1B:
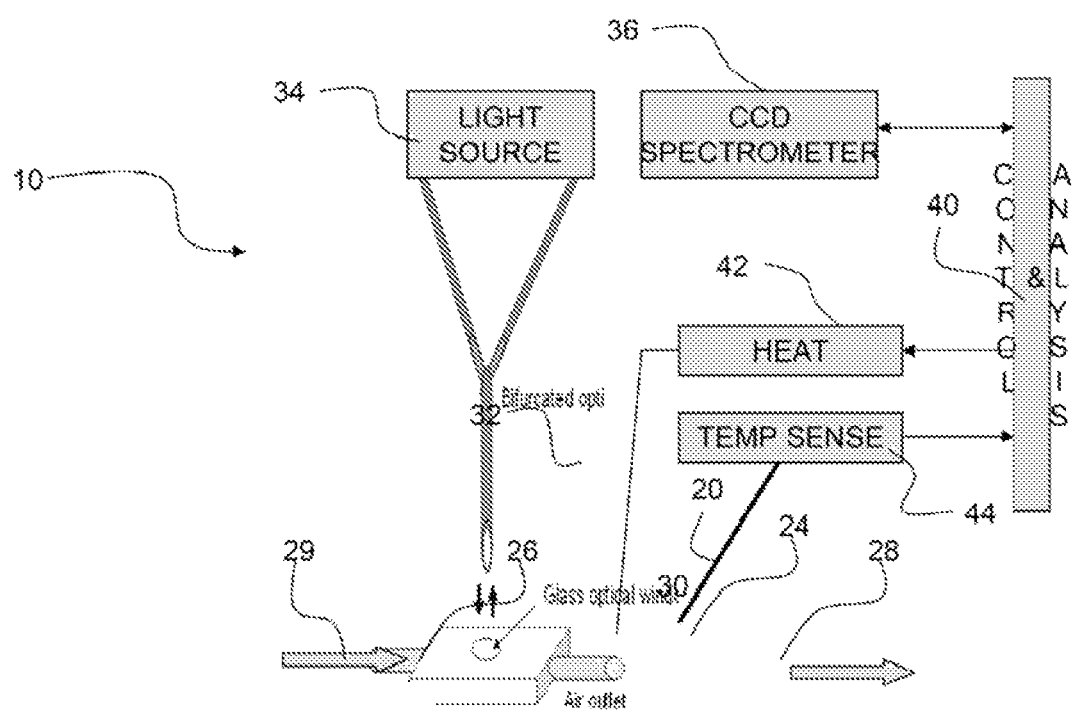
FIG. 1B illustrates a preferred system of the invention for conducting temperature response sensing and classification of molecular analytes.

FIGS. 1A-1B show a sensor system 10 and sensor 12 of the invention. FIG. 1A shows a sensor 12 used in the system 10 shown in FIG. 1B. The sensor 12 includes a porous optical film 14 that is fabricated from a semiconductor or insulator substrate 16. The substrate in this example embodiment is mounted on a resistive heater 18 that can directly heat the film 14 via the substrate 16 for thermal cycling used in sensing methods of the invention. Other heaters can be used, such as lamps, and direct printed resistive traces. A thermocouple 20 permits the temperature of the porous optical film 14 to be monitored. The porous optical film 14 can be fabricated in various materials as Si, $SiO_2$, carbonized Si, alumina, Ge, GaAs, Ti, $TiO_x$ and polymers. The selected material used to form the optical film 14 must stable optically and thermally during the sensing conditions that are employed.

Preferred porous optical films are fabricated from inorganic materials, which permit synthesis via etching. Porous silicon is a preferred material and is obtained by etching silicon electrochemically enabling easy control of the pore size and pore shape of the porous optical film and its subsequent optical properties. Thus, the porous silicon or a porous silicon derivative is preferable for a porous optical film in this invention. Oxidized silicon is preferable from the view point of stability. The porous optical film 14 can be chemically modified to target sensing specific classes of analytes or specific analytes. Potential surface chemistries include oxidized ($SiO_2$), acetylated (see, e.g., Salonen, et al, "Studies of Thermally-Carbonized Porous Silicon Surfaces," physica status solidi (a) Vol 182, Issue 1, pages 123-126, (November 2000)), freshly prepared silicon hydride, and other surface functionalizations established in the literature. See, e.g., Buriak, J. M., "Organometallic Chemistry on Silicon and Germanium Surfaces," Chem. Rev. 2002, 102(5), 1272-1308. If a porous optical film is made from an organic material, nano imprint technology is preferable to construct a porous optical film (such as in WO 2005/61379; JP2008-044283). By synthesizing the template and transferring the shape carefully, the control of pore size and pore shape of a porous optical film is achievable.

In principle, any porous optical film structure is acceptable so long as its optical properties can be monitored. Such porous optical films include Fabry-Perot, Rugate, microcavity, Bragg stack films and so on. The following examples detail the use of a one dimensional photonic crystal; however two dimensional photonic crystals, three dimensional photonic crystals and other a porous optical films can be used for the sensor element as well. The Rugate structure, consisting of a refractive index profile that various as a sinusoid, is an example of a one-dimensional photonic crystal that can be fabricated to exhibit a visible spectral peak or photonic band gap. In the case of silicon, a Rugate film can be obtained by electrochemical etching under hydrofluoric acid. The sinusoidal etching current applied can be adjusted to control pore size and pore shape of the porous optical film 14.

FIG. 1B illustrates the system 10 that includes the includes the sensor 12 that was shown in FIG. 1A within a vapor dosing cell 24. An inlet and outlet 26 and 28 permit introduction and exit of vapors/gases in a vapor stream 29 that potentially include analyte molecules to be detected by the sensing system 10. An optical window 30 permits stimulating and sensing an optical response via a bifurcated optical cable 32. A reflective spectrum is stimulated from the optical porous film 14 (see FIG. 1A) by light source 34 through the cable 32 and sensed by an optical detector, such as a CCD spectrometer 36 through the cable 32. Another example optical detector is a photodiode or array or photodiodes. Example light sources are LEDs, tungsten-halogen lamps, incandescent bulbs, and semiconductor lasers.

A controller and analysis device 40, e.g., computer, receives and analyzes the signal obtained by the spectrometer 36. The signal is sensed over a sensing time period where a thermal cycle is induced in the optical film 14 by a heat control 42 under the control of the controller 40 to heat the resistive heater (FIG. 1A). A temperature sensor 44 senses through the thermocouple 20 the temperature of the substrate 16 and film 14, which temperature information is used by the controller to control the sensing time period and relate the acquired optical data to temperature date for determining the presence and identify of analytes. The controller 40 preferably accesses a database that includes, in preferred embodiments, hysteresis curves over a heating and cooling cycle, and or changes in the wavelength position of the optical film's spectral peak(s), and rate of change, shape, or functional form of the sensor optical response.

In a preferred method of analysis, each time-chart of the shift in the spectral position of the optical band gap shows a specific response depending on each analyte. Particularly, a plot of the dosing of the sensor and its recovery by heating contains information specific to each analyte such as the rate, magnitude, and shape (second and third derivatives) of the spectral shift. Therefore, by comparing with a database of sensor responses after heating with know analytes, an unknown analyte can be identified. To identify the analyte, the sensor can be operated in various conditions; analyte can be present in the sampled atmosphere and the sensor heated under such constant analyte exposure, or analyte may no longer be present in the sampled atmosphere but remain present in and desorbed from the optical film when heated.

Any vapor analyte is detectable so long as the refractive index of the analyte is different from that of the porous optical film. For the needs of vapor sensor, the application to an organic vapor sensing is valuable, moreover alcohol sensing is one of the most feasible applications. An important feature of the invention is that methods and sensors are able to reset the sensor element quickly, even if the molecular weight of analyte is high, 100 or more, or the interaction between analyte and the porous optical film is strong. Quick recovery enables the device to be used again with less delay than a device without a recovery feature.

The resistive heater 18 (FIG. 1A) is one option for heating the porous optical film 14 by heating the substrate 16, but there are also other options for providing the localized heating of the film 14 in a manner preferably selected to avoid heating the vapor stream. To heat effectively and to control temperature carefully, a heater should be mounted in close proximity to the porous optical film 14. A resistive heater in contact with the backside of the porous optical film and a lamp providing infrared heating to the backside of the porous optical film are example suitable heaters.

Other prior approaches for heating porous films can be used. Such approaches include applying a thermal pulse include direct contact with a thermoelectric heater. See, Motohashi, A., M. et al., "Identification of Water Molecules in Low Humidity and Possibility of Quantitative Gas Analysis using Porous Silicon," Gas Sensor Japanese Journal of Applied Physics Part 1-Regular Papers Short Notes & Review Papers, 35(8), 4253-4256 (1996); Foucaran, et al., "Porous Silicon Layer Coupled with Thermoelectric Cooler: a Humidity Sensor," Sensors and Actuators A, Vol. 79, pp. 189-193, (2000). Another approach is on-sensor deposition of metal to form a resistive heater. See, e.g., Z. M. Rittersma, et al., "A Novel Surface Micro-Machined Capacitive Porous Silicon Humidity Sensor," Sensors and Actuators B, Vol. 68, Iss. 1-3, 210-217 (2000). Other approaches include suspended hotplates, Tsamis, et al "Thermal Properties of Suspended Porous Silicon Micro-Hotplates for Sensor Applications," Sensors and Actuators B: Chemical Volume 95, Issues 1-3, Pages 78-82 (15 Oct. 2003,) and direct electrical contact with the bulk silicon surrounding a sensor chip wherein the bulk material acts as the resistive element for heating.

As mentioned above, a thermal pulse can be applied to "reset" the porous optical film 14 by desorbing molecules from the film. The period of desorption also provides a sensing period to obtain an optical response as a function of time and temperature. The desorption temperature will depend upon the analytes that are of interest for detection, but heating to 60° C. or more is preferable in many cases. The effect of the heating depends on both the heating profile, including the rate of heating, maximum temperature, and duration of heating, as well as on the analyte and sensor surface chemistry. Sometimes several heating pulses for one sensor reset are more effective than applying a single pulse. To reset the device completely and quickly, heating to 130° C. or more is preferable, furthermore 160° C. or more is more preferable.

Experiments have demonstrated that the thermal cycled optical response provides information characteristic of particular molecules. Experiments have also demonstrated unique thermal pulse optical responses, and the ability to reset the film during a sensing event. The experiments will illustrate preferred methods to construct a database of characteristic response curves over time and temperature that uniquely identify particular molecules.

EXPERIMENT EXAMPLES

Preparation of a Porous Optical Film

Porous silicon rugate optical films were prepared from single-crystal, (100)-oriented highly boron-doped p-type Si (Siltronix, 1-1.2 mΩ-cm resistivity) by electrochemical etching in 3:1 v:v solution of aqueous hydrofluoric acid: ethanol (49% hydrofluoric acid from Fisher Scientific, Inc). Etching was performed in a Teflon cell with a platinum mesh counter electrode and a galvanostat (Princeton Applied Research Model 363) under computer control (Lab View, National Instruments.) The current waveform was sinusoidal, with a period of 7.73 s, varying between 12.5 and 62.5 mA/cm$^2$ applied for 75 cycles, and the film was subsequently oxidized by placing said etched sensor into a tube furnace (Lindberg Blue) for 45 minutes at 800° C. resulting in Rugate peak at ~570 nm. After that the sample was allowed to slowly cool down.

The current density waveform of the Rugate etch was varied in time (t) sinusoidally according to:

$$I(t) = I_{min} + \frac{\Delta I}{2}\left[\sin\left(\frac{2\pi t}{p}\right) + 1\right] \quad (1)$$

where $I_{min}$=12.5 mA/cm$^2$ and $\Delta I$=50 mA/cm$^2$ with a period of p=7.73 s.

The density of the films used in experiments was determined by dissolving the porous layers and conducting gravimetric determination. Oxidized optical sensors had an average porosity of 29%+−2% for 5 oxidized samples. Scanning electron microscopy was used to determine porous silica layer thickness by cutting and imaging cross sections with a Phillips XL30 Field Emission ESEM in secondary electron mode and an accelerating voltage of 10 kV. Oxidation of the porous layer and its surface stability before and after thermal cycling and vapor dosing was verified through attenuated total reflectance FTIR spectroscopy. Spectra were recorded with a Thermo Scientific Nicolet 6700 FTIR with a Smart iTR diamond ATR attachment using a resolution of 2 cm$^{-1}$ and an average of 128 scans. Nitrogen adsorption-desorption isotherms of the porous SiO$_2$ were recorded at 77 K using a Micromeritics ASAP 2010 volumetric apparatus. Samples were first degassed in situ at 323 K until a static vacuum of 5×10$^{-5}$ Torr was reached. Pore dimensions were determined using the BdB method. An opening pore diameter of 4.9 nm and average pore diameter of 5.9 nm were determined.

The porous optical film was mounted in a Teflon cell with a glass slide, sealed with kapton O-rings. A thermocouple was attached to the end of the surface of a porous Rugate film and a flat thin film heater was attached in the backside of etched film (Minco) consistent with FIGS. 1A and 1B. Reflected light spectra were acquired through the glass.

An electronic flow meter (Alicat Scientific Inc.) was used to keep the flow rate at 500 sccm throughout the example experiments. The flow was split into two lines, one carrying pure medical air and the other passing medical air through a bubbler of analyte vapor. A valve selected delivery of either analyte in air or pure air to the sensing chamber. The bubbler of analyte vapor was placed in a constant temperature water bath kept 25-27 C to control the analyte vapor pressure.

The vapor delivery system consisted of two electronic mass flow controllers (Alicat Scientific) pooled into a vapor delivery line and two controllers pooled into a nitrogen line. The Teflon tubing of the vapor line flowed horizontally into a heated stainless steel vaporization block maintained at 50° C. to promote full vaporization. Peek tubing from the outflow of a low-flow liquid pump (MilliGAT 6 nl-10 ml/min, Glbal-FIA) was inserted into a vertical tap in the heated block fitted with Swagelok seals to inject analytes into the flow stream, with the calibrated pump rate of liquid analyte delivery and nitrogen flow rate determining the vapor concentration. Solenoid valves before and after the block prevented back pressure to the flow controllers. The outflow of the vaporization block was united with the nitrogen flow line at a computer controlled four-way valve, with the nitrogen and vapor lines switched between two valve outlets, one to the flow cell and the other to a waste stream. Both lines were maintained at a flow of 1 L/min. Vapor concentrations were validated with a gas chromatograph (SRI Instruments 8610C with FID detector).

The backside of the sensor chip was coated with thermal paste (AOS Thermal Compounds) and placed on a thermoelectric Peltier module driven in pulse width modulation mode by a PID controller unit (Ferrotec FTC100), with a copper block heat sink and an aluminum, fan-cooled heat sink underneath the thermoelectric. Isothermal experiments utilized the PID controller algorithm to maintain temperature within 0.1° C. For temperature cycling, the copper block was removed and the controller unit placed in manual mode, with a serial connection executing power control through LabView. A thermocouple was placed on the silicon top surface of the sensor chip with Kapton high temperature tape (VWR) outside of the optical interrogation area. A thermistor affixed to the thermoelectric Peltier was used to validate thermocouple readings The thermocouple temperature reading was converted to voltage (Omega TAC80B-K) and amplified (Stanford Research SR560 low noise preamplifer) before DAQ acquisition into LabView. The sensor's vapor flow cell was consistent with FIG. 1B and consisted of a Teflon cell with Swagelok input and output ports and a glass optical window to allow optical interrogation of the sample. A Kapton O-ring on top of the sample sealed the sensor to the glass window.

Reflected light spectra of the samples in the visible region were taken from 345-1045 nm with a CCD spectrometer (Ocean Optics USB4000) with a tungsten-halogen light source (Ocean Optics LS-1) connected with a Y-branch 600 um diameter, bifurcated multimode optical fiber. The common end of the bifurcated fiber was focused with an objective lens to a 2 mm² spot size and positioned normal to the porous silica surface. Each Rugate spectrum collected was fit with a Gaussian function in LabView to determine the peak wavelength ($\lambda_{max}$). Rugate spectra and temperature readings were acquired at a rate of 5 Hz for temperature cycling runs, 1 Hz for equilibrium-shift isothermal adsorption-desorption dosing, and 9 Hz for isothermal desorption rate experiments Experiments Regarding the Effect of Heating Comparative Example 1

Figures 2A, 2B, 2C:
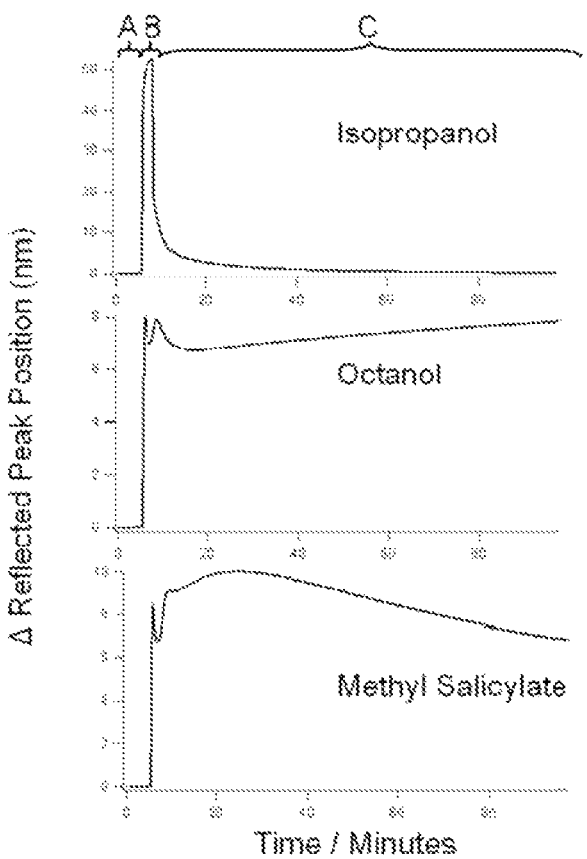
FIGS. 2A-2C are comparative experimental results showing the position of the reflected light peak of oxidized optical films as the film is exposed to isopropanol, octanol, and methyl salicylate and allowed to recover without heating.

Oxidized silicon was used as a porous optical film sensor. After 5 minutes of flowing dry air, analyte (67% vapor pressure concentration) was delivered for 3 minutes, followed by a flow of pure dry air. The position of the reflected spectral peak from the oxidized sensor chip is plotted versus time in FIGS. 2A-2C for an exposure of three separate chips to isopropanol (IPA), octanol, and methyl salicylate. The position of the reflected spectral peak from the oxidized sensor chip is plotted versus time for an exposure of three separate chips to isopropanol (IPA), octanol, and methyl salicylate. In section A, a baseline is established under a flow of medical (dry) air. In section B, the sensor chip was exposed analyte for three minutes. In section C, the sensor was allowed to recover in a flow of medical air. While IPA recovered to its initial baseline quickly, the heavier analytes octanol and methyl salicylate did not and so the sensor is not "reset" and rendered less sensitive.

Example 2

Figure 3A:
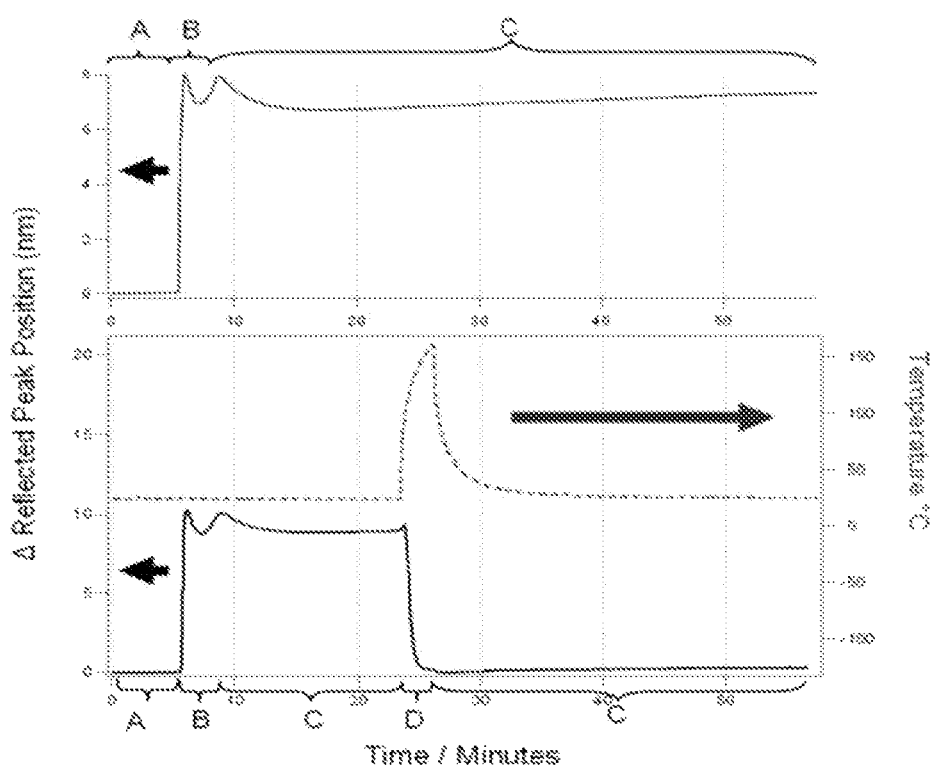
FIGS. 3A and 3B are graphs of experimental results showing time-charts comparing the recovery of oxidized optical films in air without heating, after their exposure to analytes, to their recovery aided by a thermal pulse.
Figure 3B:
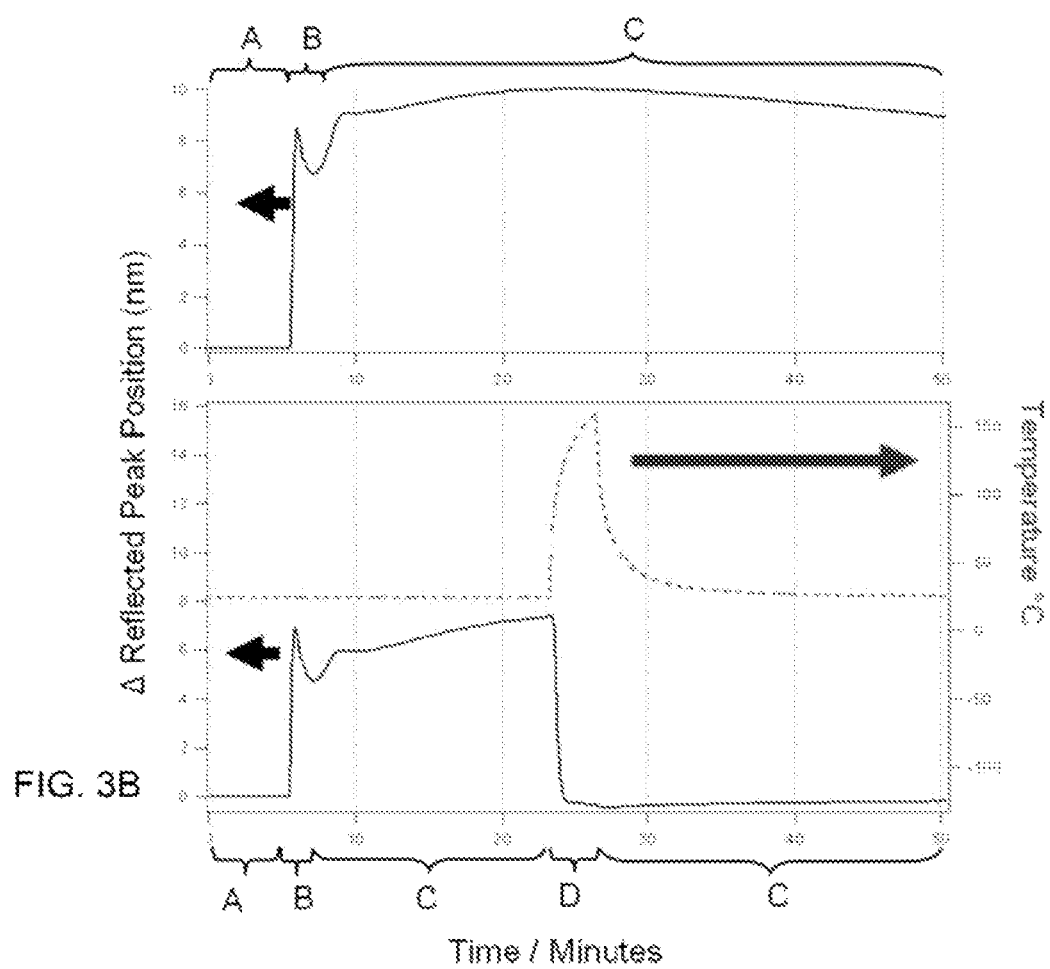

The oxidized silicon was used as a porous optical film sensor. As in example 1, after 5 minutes of flowing dry air, analyte (67% vapor pressure concentration) was delivered for 3 minutes, and then changing back to a flow of dry air. After 15 minutes dry air flowing, heating to 160 C was applied. FIG. 3A and FIG. 3B show time-charts of the shift in the spectral position of the optical band gap and the change of temperature. The top graphs are cropped from FIGS. 2A-2B with segments A, B, and C the same. In the bottom graphs, the baseline (segment A) and three minute analyte dose (segment B) mirror the upper graphs. These sensors were then allowed to recover for 15 minutes (segment C). In segment D, however, a thermal pulse was applied, heating the sensor chip to 160° C. A thermocouple attached to the top side of the porous Si was used to log the temperature of the sensor chip, shown in dotted line (right axis). The analyte in FIG. 3A is octanol and the analyte in FIG. 3B is Methyl Salicylate;

The bottom graphs, where a pulse of heat was applied to reset the sensor, is in contrast to the upper graphs taken from comparative example 1, in which no heat pulse was applied after the analyte exposure. For both analytes evaluated, the thermal pulse rapidly reset the response of the sensor to its initial baseline. These results show that analyte which slowly desorbs from the porous optical film could be desorbed by heating.

The level of heating was also changed. In additional experiments, the heating temperature was changed to 130° C. or 140° C. Reset of sensor was achieved by both temperatures, revealing the surprising result that it is not necessary to heat the porous optical film above the boiling point of analyte to achieve reset. It is noted that higher temperatures produce a quick reset of the device, and heating to around 160° C. or more was better so long as the photonic crystal tolerated the temperature cycling without altering its optical characteristics. Oxidized porous silicon is preferred for its durability in this respect.

Example 3

Figure 4A:
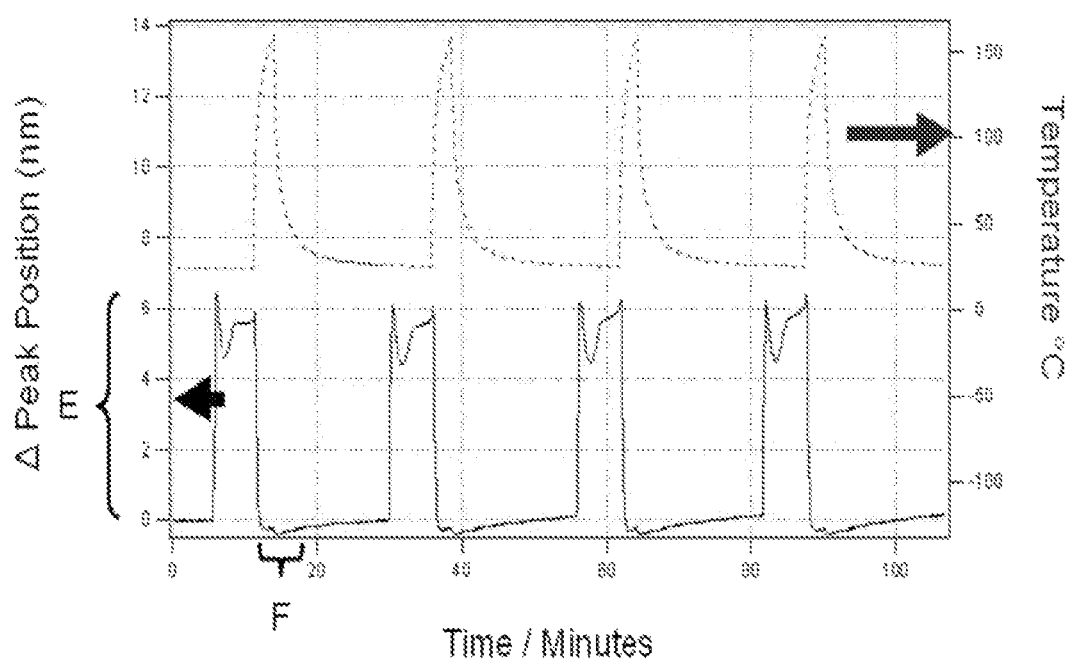
FIGS. 4A and 4B are graphs of experimental results showing time-charts displaying a repeated series of exposing the porous optical film to analyte vapor followed by recovery using a thermal pulse.
Figure 4B:
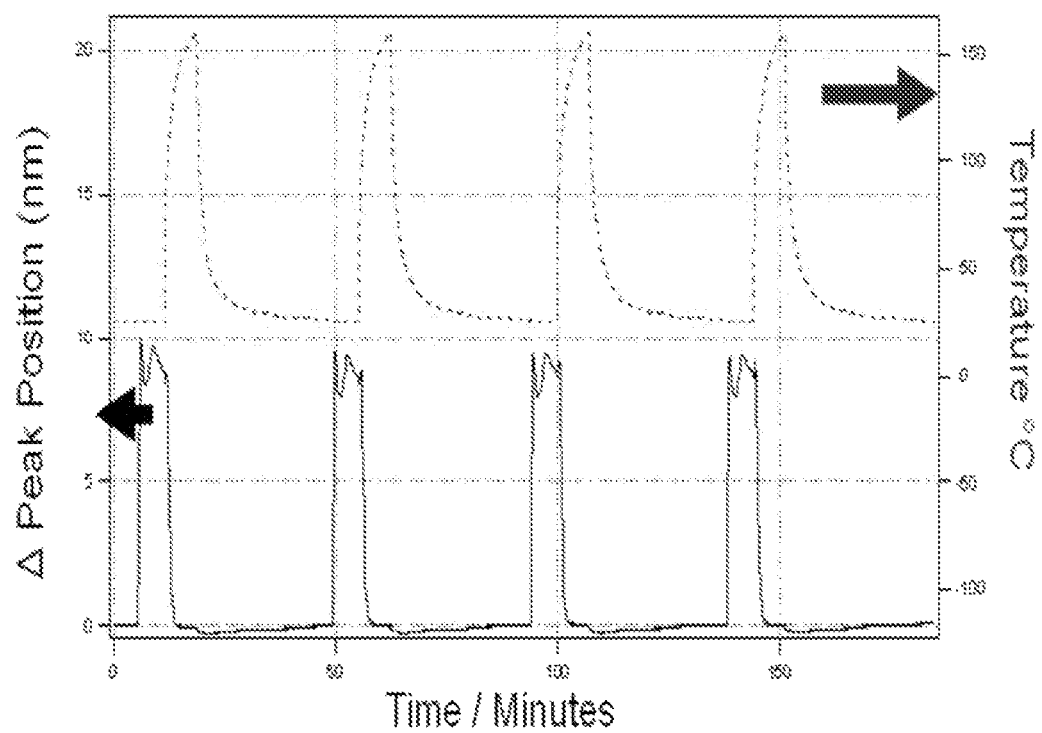

Oxidized silicon was used as a porous optical film sensor. After 5 minutes of flowing dry air, analyte was flowed for 3 minutes, followed by a flow of pure air. Then, after 3 minutes of this dry air flowing, the sensor was heated to 160° C. and allowed to cool. Once the sensor cooled to 26° C., another cycle of dosing in air, flowing pure air, and heating was performed and the sequence repeated. FIGS. 4A and 4B show time-charts of the shift in the shape of the photonic band gap and the change of temperature. The sensor demonstrates good repeatability in its response and its recovery to baseline. The magnitude of the sensor response to analyte is marked as E in the figure, and the shape and slope of the response when heated is marked as the interval F. These parameters can be used to build a database of response parameters that uniquely identify a class of vapors of specific vapors. An unknown vapor may then be identified by referencing this database of optical shift parameters.

Example 4

Figure 5:
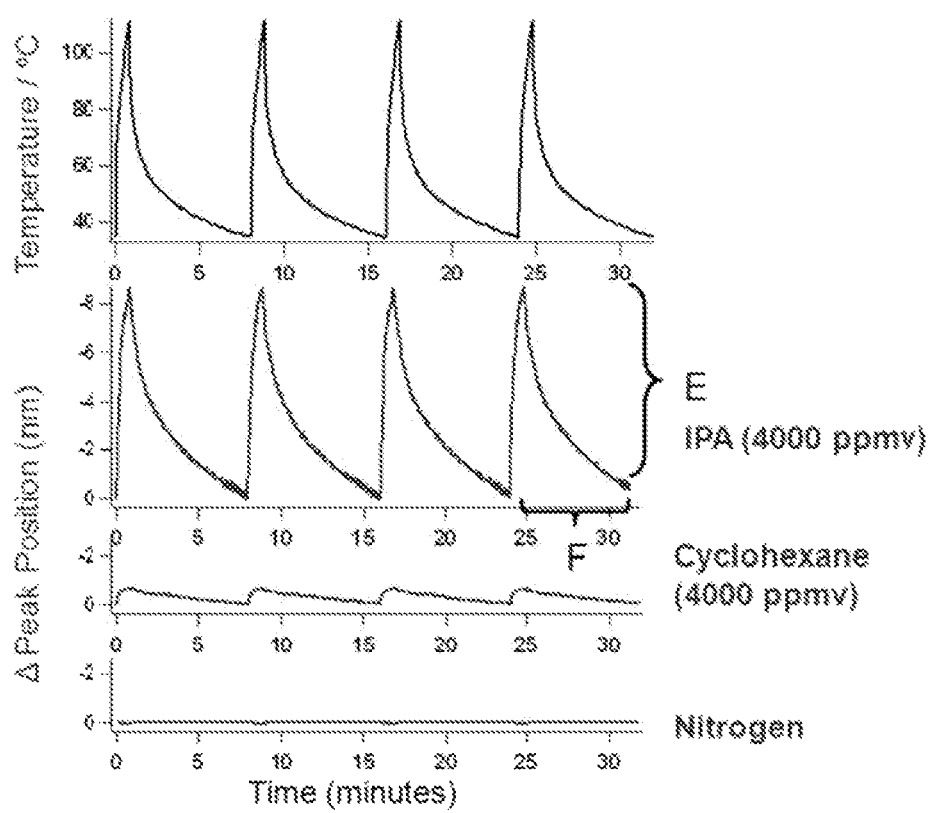
FIG. 5 is a comparison of experimental results of timecharts of an oxidized porous film heated remotely, via infrared heating of its backside, while under a constant flow of various analyte vapors.

Oxidized porous silicon optical film was heated under a constant flow of vapor analyte to demonstrate the ability to acquire spectral information about various analytes by applying thermal pulses. FIG. 5 shows the results in comparison. The chip temperature is shown in the topmost graph. The response of the sensor chip under nitrogen is shown as a reference at the bottom. As in FIGS. 4A and 4B, the magnitude of the sensor response to analyte is marked as E, and the shape and slope of the response when heated is marked as the interval F above.

The data was obtained when a halogen lamp was used to heat the backside of the sensor chip at a distance of approximately 5 cm, and the sensor chip was exposed to a constant flow of analyte in nitrogen, instead of the on-off flow used to obtain the data for the above discussed in examples in FIGS. 2A-4B. The responses to isopropanol and cyclohexane demonstrate that purging the analyte stream with air or nitrogen is not necessary to operate the sensor when heating of the sensor is used for a thermal reset and for an optical sensing period. Instead, the experiments show that an applied thermal pulse can be utilized to obtain sensor information about the analyte during the heating and subsequent cooling of the optical film, which also resets the film for continued use as a sensor.

As demonstrated by these results, the reset of the sensor is achieved effectively by heating to a desorption temperature, while information regarding the rate, shape, and magnitude of the optical shift is collected during heating and subsequent cooling. Thus, the sensor device is ready to be reused upon completion of a sensing event. The experiments also showed that oxidized silicon was more stable than silicon for photonic crystal compared to freshly prepared porous silicon.

Example 5

Isothermal Equilibrium Spectral Shifts

In these experiments, the sensor was held at a constant temperature and exposed to vapors of volatile analytes to probe the effect of temperature on the vapor porous silica adsorption equilibrium. Wavelength shifts of the Rugate stop band were first assessed at 25° C. over a full range of vapor pressures, from pure nitrogen to vapor saturation, and for the analytes isopropanol, heptane and cyclohexane. A flow of 1 L/min of nitrogen was passed over sensor. The pressure of the vapor in the flow stream was incrementally increased to saturation and likewise decreased, with the sensor response allowed to equilibrate to a steady level at each concentration. Spectra were acquired once per second and the average equilibrium Rugate central peak position for each concentration segment was determined.

The results are illustrate in FIGS. 6A-8C. FIGS. 6A, 6B and 6C show that at 25° C. the vapor concentration was progressively increased step-wise to saturation, then decreased step-wise, with the sensor allowed to equilibrate to each concentration step for Isoproponal, Heptance and Cyclohexane. Pressures are the analyte partial pressures in the applied nitrogen stream, with the total pressure of the stream at ambient The equilibrated sensor response, taken as the shift of the rugate peak wavelength at a given vapor concentration relative to the peak position during an initial baseline in nitrogen, is plotted against vapor concentration for each analyte. The step-wise cycle of adsorption and desorption of vapors was performed twice for each analyte, with the difference in datasets below the error band of each concentration segment.

FIGS. 6B, 7B, and 8B show that at three temperatures for each analyte, the concentration was progressively increased to 7.5 Torr then progressively decreased, to obtain equilibrium spectral shifts at each pressure. The solid lines are fits of the data to the Toth temperature dependent isotherm equations.

FIGS. 6C, 7C, and 8C show that using the Toth isotherm fits, the spectral shifts as a function of temperature were calculated for various analyte pressures. The differences with temperature of these curves verifies the capability of an optical discrimination methodology based on modulating the temperature of the sensor As shown in FIGS. 6A, 7A, and 8A, the porous silica exhibits a type IV isotherm with an H2 hysteresis loop, which is common for mesoporous materials. The initial rise with increasing concentration corresponds to monolayer absorption, with the upwardly sloped initial linear region indicating multilayer adsorption followed by a sudden increase in adsorption due to capillary condensation. Approaching saturated vapor concentrations, the sensor response plateaus at the analyte saturated vapor pressure since the analyte sorption is limited by the finite open pore volume of the solid porous matrix. The hysteresis in porous adsorbents commonly derives from interconnected, networked pores and from the inkbottle shape of the pores, where desorption from wider sections of a pore cannot occur until desorption from the narrow neck above takes place at a lower vapor partial pressure. The corrugated pores of the Rugate porous silica layer exacerbate these constriction effects. Cyclohexane and heptane also exhibit a degree of low-pressure hysteresis, which may indicate a degree of irreversible uptake of the analyte from the smallest pores for concentrations above the capillary condensation point. The large separation between absorption and desorption segments characteristic of the H2 loop indicates a disordered pore system with a nonuniform distribution of pores sizes. This nonuniformity of electrochemically fabricated porous silica is well known and was confirmed experimentally through SEM plan-view imagery of the sensor surface and through nitrogen absorption BET analysis, in which the porous silica layer exhibited a 49 Angstrom opening pore diameter and 59 Angstrom closing diameter.

The sudden decrease in sensor response with decreasing partial pressure in the desorption curve is ascribed to the disappearance of the liquid meniscus from sudden vaporization of the condensed liquid between adjacent pore walls, leaving an adsorbed multilayer. This closure point corresponds to the Kelvin diameter d, expressed as $$d = -\frac{4\gamma M}{\rho RT \ln\left(\frac{p}{p_0}\right)} \quad (2)$$

where $\rho$, $\gamma$, and M are the vapor density, surface tension, and molecular weight of the analyte, $p_0$ is the saturation vapor pressure, and p the applied pressure. Using the known relevant physical properties of each analyte, the Kelvin diameter for the partial pressure of the inflection point of each analyte's desorption curve were calculated as 1.8, 1.8, and 1.6 nm for the respective observed desorption partial pressures of 0.3 $P/P_{sat}$ for cycloxane, 0.27 $P/P_{sat}$ for heptane, and 0.45 $P/P_{sat}$ for isopropanol. Given the nitrogen desorption opening pore diameter of 4.9 nm, this implies a multilayer thickness immediately after the desorption drop of approximately (4.9−1.8)/2=1.6 nm on the pore wall. A simple multipoint BET fit was also performed on the isothermal, equilibrated vapor dosing data in FIGS. 6A, 7A and 8A in order to determine the BET constant, $C_{BET}$. The BET constant represents the affinity between the vapor and the sample surface, and was determined to be $C_{BET}=66$ for nitrogen adsorption-desorption (77K under vacuum). For the vapor isothermal dosings, $C_{BET}=2$ for cyclohexane, 2 for heptane, and 220 for isopropanol. The large difference between isopropanol and the other analytes is due to the strong affinity of the polar molecule to the oxygen electrons on the $SiO_2$ surface.

Second, having characterized the sensor response at 25° C. up to saturated pressures, the sensor was next assessed from vapor partial pressures from zero to 7.5 Torr with finer steps of pressure and at three temperatures, as shown in FIGS. 6B, 7B, and 8B. These low vapor concentrations are most germane to sensing applications. Equilibrated sensor responses for vapor partial pressures incremented up to and then down from 7.5 Torr were determined over two absorption-desorption step-wise cycles for each analyte, with corresponding vapor concentrations in each cycles exhibiting differences in peak shifts less than the error band of each segment (<0.1 nm). The adsorption-desorption cycles over this concentration range showed no appreciable hysteresis, as expected since the maximum partial pressure of 7.5 Torr is well below the capillary condensation point for each analyte. Although cyclohexane and heptane both exhibited a small degree of low-pressure hysteresis for desorption from saturation (FIGS. 6A, 7A, and 8A), this hysteresis was not observed for desorption from 7.5 Torr.

The Toth isotherm is commonly used to experimentally fit complex adsorption systems. Here, a set of temperature dependent Toth isotherm equations were applied to experimentally fit the low pressure region of the equilibrium response. These fits were determined by known methods and plotted as the solid curves in FIGS. 6B, 7B and 8B and were found to fit the experimental data at each temperature well. The empirical model used permitted the calculation of the sensor response to any given partial pressure and temperature within the fitting range of 0-7.5 Torr and 25-80° C. for the fits given FIGS. 6B, 7B and 8B. The calculated shifts in the Rugate peak wavelength, from a baseline of the sensor in the absence of vapor, are plotted versus temperature in FIGS. 6C, 7C, and 8C. Curves for several example vapor partial pressures are displayed for each analyte. The empirically calculated shift in sensor response from 25-80° C. and the difference in the functional forms of these shifts between isopropanol and the nonpolar analytes supports use of temperature modulation to yield shift-temperature curves with unique characteristics for each analyte.

This was verified by rapid thermal cycling of the sensor from 25-80° C. while it was exposed to a constant flow of vapor. FIGS. 9A and 9B illustrate data obtained for continuous cycling during simultaneous spectral acquisition. FIGS. 9C and 9D illustrate 1 cycle from FIGS. 9A and 9B. The cycling was conducted for 23 pressures of the three analytes, ranging from 0-7.5 Torr. First, the sensor was cycled under a constant flow of pure nitrogen, then exposed to the same flow rate of analyte vapor in nitrogen for 8 cycles, and finally cycled again under pure nitrogen. This sequence of baseline, dosing, and purging over repeated thermal cycles is shown for one concentration of isopropanol in FIGS. 9A-9D. The thermal cycling also served to prevent vapor buildup in the porous silica matrix by repeatedly desorbing vapors. The sensor's baseline and purge ($N_2$) Rugate peak wavelengths were found to be steady across all runs, with the sensor's chemical stability verified through FTIR spectra of the sensor acquired before and after the 69 vapor exposure runs. FTIR spectra showed no discernible change in surface functionality, nor infrared stretches from any of the analytes, with the sensor's spectra dominated by a strong v(Si—O—Si) stretch at 1020 $cm^{-1}$ and a very weak v(OH) at 3350 $cm^{-1}$. By thermally cycling the sensor, the sampling rate was also increased relative to a the sensor at ambient, since no delay was necessary for the sensor to return to baseline as the vapors desorb and diffuse out of the layer. Instead, each thermal cycle acted to reset the sensor response. For example, after a dose of 3.80 Torr of isopropanol at 25° C., the time required for the sensor response to recover in nitrogen 95% to the initial baseline position was greater than the time for 9 thermal cycling events (FIGS. 9A-9D), each of which can sample a new vapor concentration or analyte.

Figures 10A, 10B, 10C:
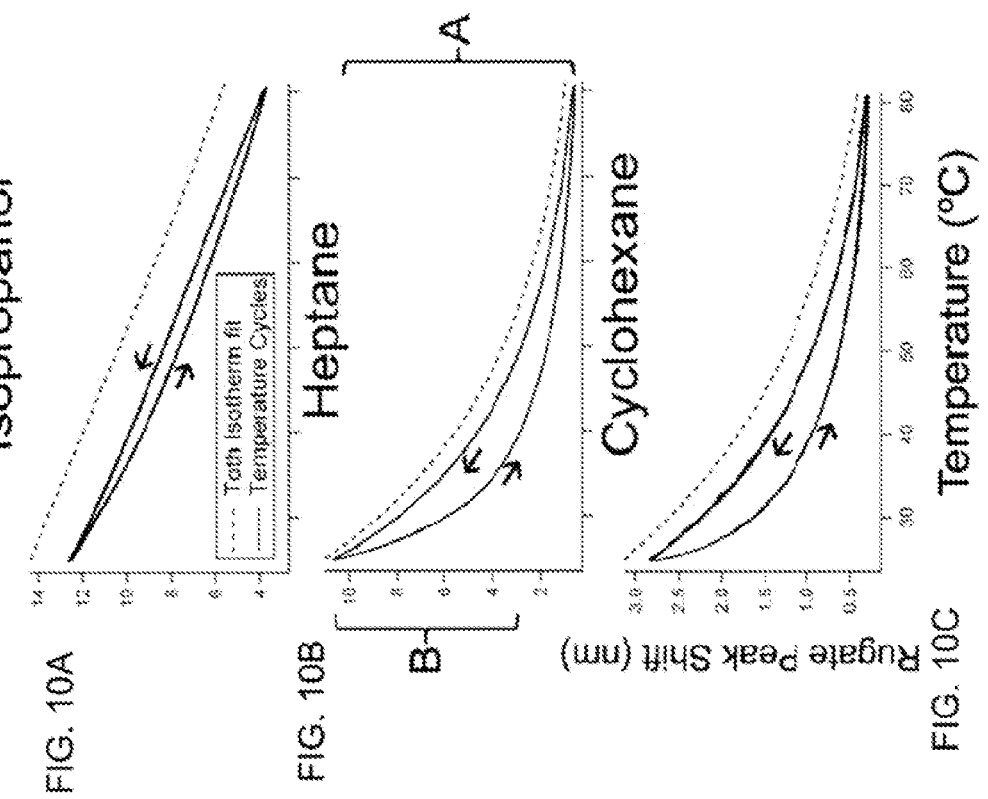
FIGS. 10A-10C illustrate the unique hysteresis spectral responses of Isopropanol, Heptane, and Cyclohexane that was demonstrated experimentally.

The unique hysteresis spectral responses of the analytes was demonstrate experimentally. FIGS. 10A-10C illustrate the hysteresis spectral responses of three analytes that was demonstrated experimentally. The plots in FIGS. 10A-10C plot Rugate peak position against temperature. The sensor baseline was taken as the Rugate peak position under pure nitrogen at 25° C. at the beginning of each run. For each plot, the last 7 cycles of the vapor exposure are overlaid, with no discernible difference between cycles. The curves represent the nominal shape of the peak shift vs. temperature for each analyte, with overlays of normalized response curves at each analyte pressure showing no deviations except at the lowest concentrations tested. For each curve, the zero point was taken as the peak wavelength under nitrogen flow at 25° C. Parameter (A) represents the spectral shift between 25-80° C. and (B) the shift between 25-40° C. Curves based on Toth isotherm fits are overlaid (dotted), representing sensor responses at equilibrium Normalization of the sensor response curves for different partial pressures of a given analyte shows little discernible difference in the shift-temperature curves from 0-7.5 Torr except at low pressures (<2 Torr) where a diffusion delay for isopropanol may be present. Arrows indicate the heating (desorption) and cooling (adsorption) branches. The curves of each vapor cycle for a given concentration of an analyte are highly repeatable, with each plot displaying an overlay of the last 7 vapor cycles of each run. The first cycle of each vapor run was excluded, since the initial portion of heating branch was not exposed to a full concentration of vapor due to a ~1 sec delay due to the length of flow cell connector tubing before vapor was passed over the sensor surface.

The empirically calculated Toth isotherm shift-temperature curves are for comparison. The shifts based on the equilibrium isotherm data collected at three temperatures follow the same functional form as the thermally cycled plots for each analyte but have a consistently greater Rugate peak shift. This is because the thermally cycled spectra are transient in temperature while the isothermal-based shifts were allowed to equilibrate to each concentration at each temperature resulting in larger adsorption and desorption shifts than the peak shifts from the unequilibrated, thermally cycled measurements.

The peak shift-temperature profiles of nonpolar heptane and cyclohexane exhibit a markedly more saddle-shaped response than isopropanol. Isopropanol's smaller decrease in sensor response with increasing temperature is consistent with its stronger interaction to the oxidized surface compared to the other analytes, since the surface is predominantly Si—O—Si with a small contribution of Si—OH surface bonds, as seen in FIR spectra of the sensor. Isopropanol is known to hydrogen bond to silica surfaces. The strong surface interaction of isopropanol results in a less dramatic shift in the sorption equilibrium with temperature than that observed with heptane and cyclohexane, as well as in a slower isothermal desorption process from the adsorbed, loaded state to the equilibrium state in nitrogen. The shift-temperature profiles of heptane and cyclohexane exhibit sharper changes in the sensor response with temperature. Since the sensor response is a measure of the amount of adsorbed analyte in the porous layer, the different sensor response profiles support a vapor-sensor sorption equilibrium dominated by analyte self-affinity in the cases of cyclohexane and heptane, compared to the surface affinity dominance of the isopropanol interaction. Indeed, the shift-temperature profiles of heptane and cyclohexane appear consistent with the exponential change in the vapor pressure of the analytes with temperature. The importance of analyte-analyte self affinity interactions in the observed behavior of the two nonpolar analytes may be due to their known lower surface affinities, particularly if multilayer adsorption occurs on preferred adsorption sites before a full adsorption monolayer is formed. At a given temperature, the sensor response to heptane is greater than to cyclohexane. This may be due in part to the known ability of the heptane molecule to conform to microporous adsorption sites on the heterogenous pore surface, while cyclohexane is more rigid and adsorbs to sites of a preferred size.

The cooling time of the thermally cycled sensor was twice the heating time. Additionally, analysis of the equilibration time of the sensor to isopropanol, tested at both 7.49 and 0.76 Torr at several constant temperatures, showed that the times taken to equilibrate from a stream of pure nitrogen to a stream of vapor (diffusion into the layer and adsorption) were less than half the times taken to equilibrate from a stream of vapor to a stream of nitrogen (desorption and diffusion out). In contrast to the heating profiles, the faster vapor uptake rate combined with the slower cooling rate of the sensor resulted in no observed deviation in the spectral shift-temperature cooling profiles of the sensor with isopropanol over the concentrations tested.

Figure 11:
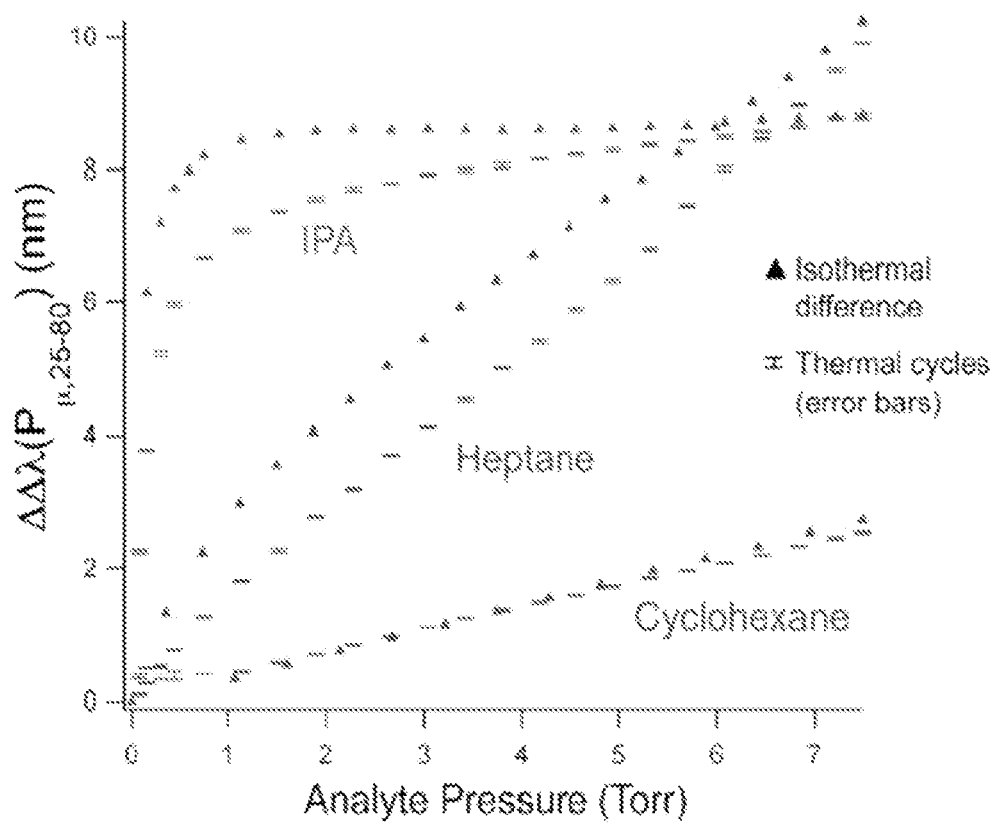
FIGS. 11 and 12 illustrate experimental data showing analyte determination at multiple temperatures and a range of pressures, showing that analytes are determined independently of concentration.
Figure 12:
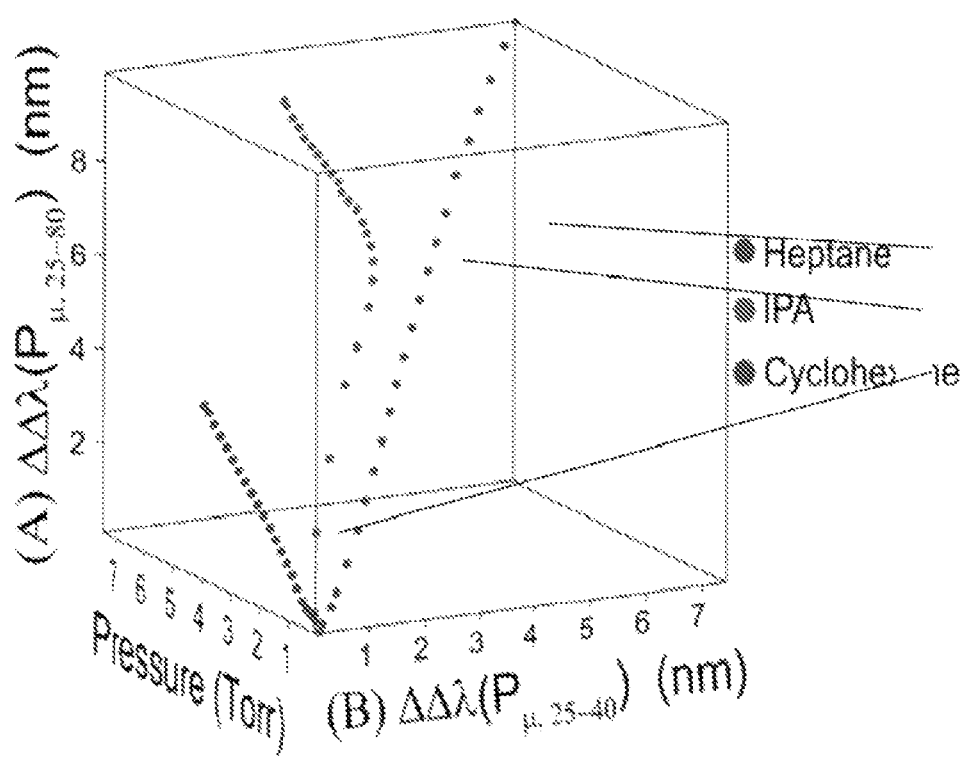

Additional experiments shown that analytes are uniquely identified even if the concentration is not known. Data was taken over a wide range of concentrations as a function or partial pressure and yielded widely separated curves over a wide range of analyte-concentration combinations. The analysis here plots the difference in Rugate peak response at two different temperatures, e.g., 25° C. and 80° C., over a range of analyte pressures, and the data reveals well separated responses, such as shown in FIG. 11. Readily discernable curves are also revealed for the same three analytes by producing a three-dimensional graph that uses two different sets of temperature differences, e.g., a first set of data at 25° C. and 80° C. and a second set of data at 25° C. and 40° C. over various pressures as shown in FIG. 12.

Determination of concentration is also possible because the size of the hysteresis loops and the relative separation or "bulge" between the heating and cooling branch is dependent upon heating and cooling rates as well as analyte concentration. In experiments, for various concentrations of analytes the heating traces are "below" the cooling traces for all 3 analytes, giving a counterclockwise sense to each heat/cool loop, as indicated by the arrows in FIGS. 10A-10C. An exception was observed However, and exception was observed at low concentrations of isopropanol, where the heating curves are "above" the cooling traces, yielding a clockwise sense to the heat/cool loop. This is shown in FIGS. 13A-13D for isopopanol. The swapping of the heat/cool ordering in the hysteresis loops was not observed for heptane or for cyclohexane, but observable changes in the response curves were present for different pressures, supporting the ability to determine concentration. In FIGS. 13A-13D the cycles were each 89 seconds in duration with 29 seconds of heating and 60 seconds of cooling.

Heating rates were also varied, and the curves change for different rates of heating. At some rate of heating, the spectral response will show a "lag" as the sensor chip warms faster than the rate limit of desorption. However, the studies showed generally that the spectral response is also dependent on the rate of heating. The spectral response for desorption isopropanol, heptane and cyclohexane was also observed by stopping analyte flow and maintaining a constant temperatures of 25, 40, 60 and 80° C. Heptane and cyclohexane desorbed significantly or completely by 2-4 seconds and showed a clear difference in optical response by that time and a constant response well before 10 seconds at all temperatures, but the time required for desorption of isopropanol was not fully purged until 29 seconds. As noted above, this is due to the different properties of isoproponal.

Example 6

Thermal Pulse Reset and Spectral Shifts

In these experiments, freshly prepared and oxidized sensors were examined, exhibiting slow desorption and retention of the vapors at ambient after 1.5 hours, but rapidly expelling vapors when heating with a thermal pulse, resetting the sensor to its baseline response. Cycles of vapor dosing, followed by thermal refreshing, were consistent and repeatable. The temperature at which the rate of the optical response was greatest was unique to each vapor expelled and differed between the oxidized and freshly prepared porous materials.

The sensors were prepared according to equation (1) above, with where $I_{min}$=12.5 mA/cm$^2$, $\Delta I$=50 mA/cm$^2$. The period was p=6.2 seconds for as-etched optical structures and p=7.73 s for the structures subsequently oxidized, so that both types of sensor material exhibited a Rugate stop band reflectance peak at the same wavelength, centered at 568 nm. Since the fresh samples oxidize upon heating, multiple samples were prepared under identical etch parameters from the same 4" silicon wafer, with a stop band central peak deviation. where $I_{min}$=12.5 mA/cm$^2$, $\Delta I$=50 mA/cm$^2$. The period was p=6.2 seconds for as-etched optical structures and p=7.73 s for the structures subsequently oxidized, so that both types of sensor material exhibited a rugate stop band reflectance peak at the same wavelength, centered at 568 nm. Since the fresh samples oxidize upon heating, multiple samples were prepared under identical etch parameters from the same 4" silicon wafer, with a stop band central peak deviation. Gravimetric porosity determination showed that five samples had an average porosity of 65% +/−2%. For oxidized samples, the different density of the oxidized (2.21 g/cm$^3$) etched layer than the bulk silicon (2.33 g/cm$^3$) must be considered. The porosity of an oxidized sample is $(V_{total}-V_{SiO2})/V_{total}$, where the total volume removed after etching and dissolution is $V_{total}=(m_1-m_3)/2.33$ and the silica volume, for a weight ($m_4$) of the porous layer after oxidation, is $V_{SiO2}=(m_3-m_4)/2.21$. Oxidized optical sensors had an average porosity of 29%+−2% for 5 oxidized samples SEM Measurement or pore size showed average pore diameters of 8 um and 6 um for oxidized and freshly prepared structures, respectively. Isoproponal recovered in about an hour after a 3 minute exposure, but after 12 hours, MeS samples recovered to 5-10% above the initial baseline.

Tests were conducted without a thermal pulse, wherein freshly etched and oxidized optical sensor films were exposed to isoproponal, methyl salicylate (MeS) and octanol and allowed to recover in dry air. Octanol samples showed significantly less recovery, decreasing to only 25-35% above the initial baseline after 12 hours day at ambient. The presence of these trapped vapors after long recovery periods was confirmed by FTIR. Freshly prepared samples show significantly faster recovery of both analytes than oxidized samples. This is due to the weaker interaction of the (Si—H) sample surface to the moderately polar analytes compared to the polar (SiO$_2$) surface, as well as from the larger pore size of the fresh samples (6 nm diameter compared to 8 nm diameter oxidized) and the thinner layer thickness of the fresh samples (12.4 um compared to 16.2 um for oxidized) that allowed for faster diffusion from the layer.

A thermal pulse was shown to be a great advantage for refresh and providing a clear optical event for analyte identification. The results for freshly prepared samples are shown in FIGS. 14A-14F and for oxidized samples in FIGS. 15A-15F.

In these figures, for each cycles the porous layers were allowed to establish a baseline in dry air for 5 min, exposed to analyte for 3 min, allowed to partially recover in air for 3 min, then heated to 160° C. and allowed to cool under dry air to 26° C. The partial recovery in air demonstrated the slow recovery of the sensor after analyte exposure for each cycle before the application of the thermal pulse. FIGS. 14B, 14D & 14F, and FIGS. 15B, 15D and 15F show the temperature-time profiles of each exposure run. In FIGS. 14E, 14F, 15E and 15F, the sensor was not exposed to vapor but was subjected to a thermal pulse and heated to 160° C. These traces display the intrinsic changes in Rugate peak wavelength due to the temperature increase, without the influence of analyte vapors. Following an initial baseline (segment A), each cycle consists of exposure to analyte for 3 minutes (B), a flow of dry air for 3 minutes (C) to demonstrate slow recovery without heating, and a thermal pulse (D) and recovery in air to demonstrate a refresh of the sensor response. For octanol (middle panels), an additional heat pulse was applied after the last dose-heat cycle to desorb trapped vapor from the layer.

The change in spectral position of the Rugate peak when heated after vapor exposure, labeled as section D, exhibits a hook shaped response for the fresh (Si—H) sensor surface and a smaller response spike for the oxidized surface. These features are due to the intrinsic change in the spectral band when heated. As the sensor temperature increases, vapors are expelled and a large reduction in the peak position is observed, but as the temperature continues to increase the peak position increases due to the refractive index change of the porous layer with temperature. This intrinsic change recovers to the initial ambient baseline as the sensor cools. The freshly prepared porous silicon samples also display decrease in the spectral peak position after each cycle of heating, for both the MeS vapor-dosed run and the cycles in which only heating was applied with no vapor dosing. This spectral blueshift is due to an increased rate of oxidation of the porous silicon at elevated temperatures, as conversion of porous silicon to silica lowers the average refractive index of the optical layer.

The freshly prepared, porous silicon sample exposed to octanol exhibits a baseline increase with each vapor cycle, indicating that the refresh temperature-time profile was not sufficient to thermal reset the sensor response. An additional thermal cycle after vapor exposure, FIGS. 14E, 14F, 15E, 15F, was sufficient to decrease the sensor response to baseline level before the cycle of vapor exposure and heating, and as expected, thermal pulses to higher temperatures and for longer times resulted in complete removal of octanol from the layer, with two cycles to 190° C. with the same heater configuration fully expelling octanol from the sensor, confirmed by FTIR. Testing showed that sensing low volatility vapors without thermally refreshing results in a steady accumulation of analytes and a loss of the sensor's dynamic range after multiple analyte exposures. This would interfere with sensing and detection. The sensor inherent response without analyte showed that the sensors exhibits its own peak shift. Since the fresh sample oxidizes at higher temperatures, the cooling cycle follows a curve at a lower response than the heating segment. Oxidization is not linear with temperature and occurs faster at higher temperatures, consistent with the observed linearity of the sensor shift vs temperature response deviating most above 140° C. due to increasingly faster oxidation. The spectral response to temperature was determined by fitting each curve between 40 and 140° C., with values of d$\lambda$/dT given in Table 1.

Thin film interference fringes of the spectra, were utilized to calculate the change in optical thickness with temperature, d(2n$_{avg}$L)/dT, by performing a Fourier transform of each spectrum in the vapor exposure runs to determine the effective optical thickness 2n$_{avg}$L at each time point. Traces of 2n$_{avg}$L versus temperature were then fit between 40 and 140° C., where L is the cross sectional layer thickness and n$_{avg}$ is the average refractive index of the porous layer

TABLE 1

| Measured optical response to heating[1] | | |
|---|---|---|
| | Fresh (Si—H) | Oxidized (SiO$_2$) |
| d$\lambda$/dT | $2.8 \times 10^{-2}$ | $3.7 \times 10^{-3}$ |
| d(2n$_{avg}$L)/dT | 2.8 | 0.60 |
| n$_{material}$ (Si or SiO$_2$) at 25° C. | 4.3 | 1.46 |
| dn$_{material}$/dT (Si or SiO2) | $5.1 \times 10^{-4}$ | $1.2 \times 10^{-5}$ |

[1]$\lambda$ is in nm, T in ° C.

FIGS. 16A-D show one cycle of thermal refresh of spectral shift versus temperature. The spectral shifts versus temperature are shown for one cycle of vapor dosing followed by heating. Vertical lines at the left of each panel are the spectral shift at 25° C. upon vapor exposure, followed by a partial decrease of the peak position in the 3 minutes of post-exposure air flow before heating. The temperatures of the maximum heating rate, determined by the second derivative of the curves, are indicated. Dotted lines indicate spectral data with no correction for the native change in spectral position with temperature. Solid lines are the peak positions with temperature corrected for the observed native shifts. FIGS. 16A and 16C illustrate data from porous SiO$_2$ exposure to methyl salicylate (left) and octanol (right). FIGS. 16B and 16D illustrate data from freshly prepared porous Si exposure to the analytes.

Using those calculated temperature coefficients, the spectral peak position was corrected by $\lambda_0' = \lambda_0 - (T - T_{25°})(d\lambda/dT)$, where $\lambda_0'$ is the corrected spectral position, $\lambda_0$ the spectral position at 25° C., and T the temperature. Corrected curves are displayed as solid lines, with uncompensated profiles displayed as dashed lines. The initial vertical increase in response at 25° C. In each panel corresponds to the increase in spectral position upon vapor dosing, and is followed by a slight decrease during the 3 minute recovery period in air that took place after dosing but before heating. The spectral position shift with temperature is seen as the horizontal segment of each trace that extends rightward from the vertical line of initial vapor response.

The second derivative of these curves represents the maximum rate of change of the spectral position with temperature. Since uniform thermal profiles were applied to each run, this characteristic desorption temperature can be compared for each analyte/material pair. As seen in the data, the temperature of the maximum rate of sensor shift for the freshly prepared sensor was T=72° C. for MeS and T=79° C. for octanol. The corresponding characteristic temperatures for the oxidized porous silica were significantly higher, with T=105° C. for MeS and T=113° C. for octanol. As with the differences in the ambient temperature desorption curves discussed above, the higher characteristic temperatures of the oxidized porous silica, compared to the freshly prepared material, are due to the stronger interaction of the oxygen atoms in the ($SiO_2$) surface with the polar analytes than the interaction of the weakly polar (Si—H) porous silicon. The higher temperatures could also be due to the increased Van der Waals forces exerted on the analytes condensed as liquids or adsorbed as multilayers in the porous silica due to its smaller pore diameter of 6 nm, compared to 8 nm for the freshly prepared porous silicon. The smaller pore size of the oxidized material is also consistent with its sharper temperature transition, with the change in sensor response at the characteristic temperature occurring over a smaller temperature range than the freshly prepared sensor, as seen in the data. Characteristic temperatures T at which $d^2\lambda/dT^2=0$ were calculated for the other cycles in each run and for the uncorrected spectral shift profiles, and found to agree within +/−1° C. for the oxidized runs and +/−2° C. for the runs with freshly prepared porous Si, with the greater variability of the latter resulting from gradual oxidation with each temperature cycle.

Figure 17A:
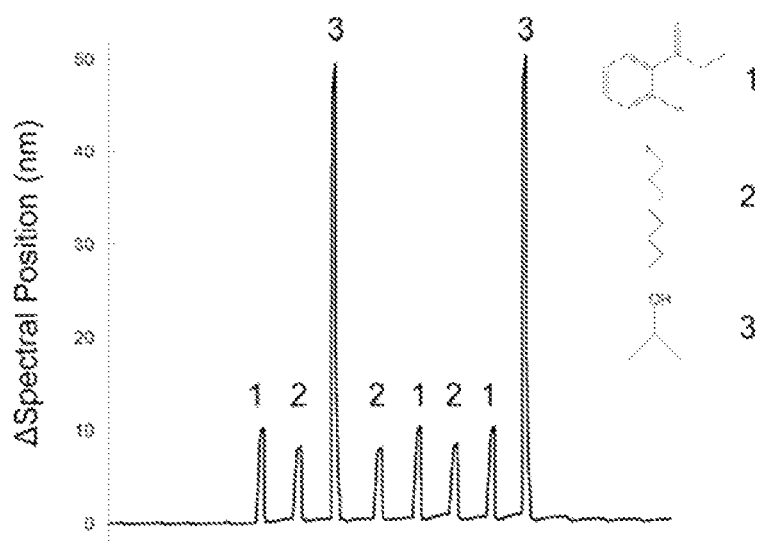
FIGS. 17A and 17B show experimental data illustrate the application of periodic thermal pulses were applied to an oxidized silicon sensor under with sequential introduction of different analytes.
Figure 17B:
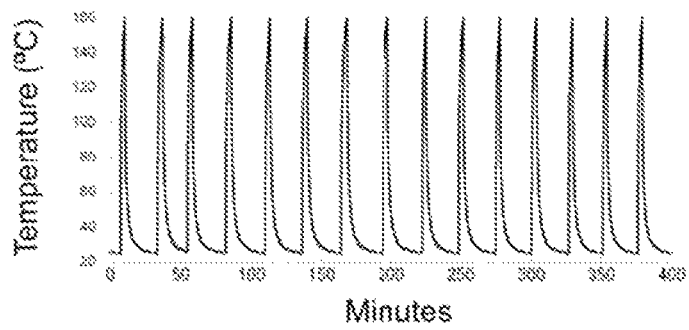

The stable baseline of the oxidized porous silica sensor over repeated thermal cycles and vapor exposures makes it suitable as a durable sensing material. Periodic thermal pulses were applied to the porous silica sensor under dry air, as shown in FIGS. 17A and 17B. The sensor was then subjected to cycles of analyte exposure and thermal refresh, alternating between isopropanol, methyl salicylate, and octanol. Each cycle of vapor exposure consisted of exposure to analyte for 3 min, recovery under dry air for 3 min, and application of a thermal pulse to 160° C. The temperature-time profile is displayed in FIG. 17B with the optical response in FIG. 17A. The recovery and optical response are both demonstrated to be excellent and different optical response are observed for each analyte. Additional tests with ATR-FTIR analysis showed that oxidized sensor chips could be reused for multiple runs, with no change in FTIR features after multiple thermal refresh cycles, the fresh sensor chips oxidized in air with each thermal pulse and required separate, identically etched samples for each new vapor run, and confirmed that the failure to reset results in accumulated additive response. The results are shown in FIGS. 18A-18H.

All exhibit peaks from the $\nu(SiH_x)$ stretches at 2112 and 2087 $cm^{-1}$, $\delta(SiH_2)$ at 907 $cm^{-1}$, and $\delta(SiH_x)$ at 623 $cm^{-1}$. Cycled heating of the fresh sample, without any exposure to vapor, resulted in the growth of a $\nu(SiO)$ band at 1009 $cm^{-1}$ as shown in FIGS. 18B and 18F. While dosing the fresh sensor with MeS and applying thermal refresh pulses yielded the same result of slight oxidation, dosing with octanol and applying a single thermal refresh pulse after each dose showed additional infrared peaks that correspond to the octanol not desorbed from the porous matrix in FIGS. 18C and 18G ($\nu(CH)$ at 2855, 2922, and 2958 $cm^{-1}$ and $\delta(CH)$ at 1466 $cm^{-1}$). When additional thermal pulses to the same temperature were applied after octanol vapor exposure, the analyte was effectively desorbed and the FTIR peaks of octanol in the sensor eliminated (FIGS. 18D and 18H). FTIR spectra of the fully oxidized porous silica are shown in FIGS. 18E-18H, and exhibit a strong $\nu(Si—O—Si)$ stretch at 1020 $cm^{-1}$. Heating of the oxidized sample without exposure to analyte yielded the same spectrum as heating the sensor after exposure to analyte.

In contrast, FTIR spectra of the sensor after the vapor accumulation runs in which no thermal refresh was applied exhibit additional infrared peaks corresponding to adsorbed analytes, as shown in the "no reset" data of FIGS. 18G and 18H. The spectrum after octanol accumulation exhibits alkyl stretch peaks[45] $\nu(C—H)$ at 2858, 2928, and 2960 $cm^{-1}$ and that of MeS after accumulation exhibits a $\nu(C=O)$ stretch[46] at 1680 $cm^{-1}$, $\nu(Ph)$ at 1616, 1587, 1487, 1444, and 1306 $cm^{-1}$, and $\delta(OH)$ at 1334 $cm^{-1}$. The FTIR spectra of liquid octanol and MeS are displayed in FIG. 10, with key peaks that were exhibited in the spectra above labeled: $\nu(CH)$ at 2853, 2924, and 1464 $cm^{-1}$, $\delta(CH)$ at 1464 $cm^{-1}$, and $\nu(OH)$ at 3325 $cm^{-1}$ for octanol; $\nu(C=O)$ at 1673 $cm^{-1}$, $\nu(Ph)$ at 1616, 1584, 1484, 1439, and 1302 $cm^{-1}$, and $\delta(OH)$ at 1334 $cm^{-1}$ for MeS.

Porous silicon and silica Rugate optical layers thus exhibited retention and slow desorption of methyl salicylate and octanol vapors at ambient temperature. Application of a thermal pulse rapidly refreshed the oxidized silica sensors to their initial baseline, and refreshed the freshly prepared silicon sensors to a lowered baseline due to thermal oxidation. For porous silica, the thermal refresh methodology was repeatable and consistent over multiple cycles of vapor exposure and thermal refresh to 160° C. The temperature at which the maximum rate of sensor response occurred was unique to each vapor and sensor material combination, supporting the ability to discriminate vapors through optical sensing of the porous layers during the thermal refresh. Periodic thermal pulses allowed for the continuous detection of sequentially administered methyl salicylate, isopropanol, and octanol vapors that would otherwise not fully desorb from the porous layer in the sensor sampling period While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A method for sensing vapor, comprising steps of:
   exposing a porous optical film to vapor which contains analyte;
   heating the porous optical film;
   monitoring an optical response of the porous optical film for a sensing time period during said heating; and
   determining identity or quantity of the analyte from a response curve obtained during the sensing time period of said monitoring, wherein said heating comprises heating to a desorption temperature and the sensing time period covers a period of desorption.

2. The method of claim 1, wherein said determining determines identity and quantity of the analyte.

3. The method of claim 2, further comprising ceasing said heating after a heating time period to cycle the porous optical film over a heating cycle and cooling cycle, wherein said sensing time period encompasses at least a portion of said heating cycle and said cooling cycle.

4. The method of claim 3, wherein said determining comprises determining a hysteresis curve from the optical response and comparing the hysteresis curve to a set of predetermined curves developed and stored in advance.

5. The method of claim 4, wherein said heating is conducted over temperature range below about 200° C.

6. The method of claim 1, wherein said heating is conducted over temperature range below about 200° C.

7. The method of claim 1, wherein said monitoring includes monitoring optical peaks and shifts of the optical peaks over the sensing time period and said step of determining determines identity or quantity of analyte from the shifts of the optical peaks.

8. The method of claim 1, wherein said porous optical film comprises silicon.

9. The method of claim 8, wherein said porous optical film is a photonic crystal.

10. The method of claim 1, wherein said porous optical film comprises oxidized silicon.

11. The method of claim 1, further comprising a step of changing the vapor pressure during said monitoring.

12. A method for sensing vapor, comprising steps of:
exposing a porous optical film to vapor which contains analyte;
heating the porous optical film;
monitoring an optical response of the porous optical film for a sensing time period during said heating; and
determining identity or quantity of the analyte from a response curve obtained during the sensing time period of said monitoring, further comprising ceasing said heating after a heating time period to cycle the porous optical film over a heating cycle and cooling cycle, wherein said sensing time period encompasses at least a portion of said heating cycle and said cooling cycle.

13. A method for sensing vapor, comprising steps of:
exposing a porous optical film to vapor which contains analyte;
heating the porous optical film;
monitoring an optical response of the porous optical film for a sensing time period during said heating; and
determining identity or quantity of the analyte from a response curve obtained during the sensing time period of said monitoring, wherein said determining comprises determining a hysteresis curve from the optical response and comparing the hysteresis curve to a set of predetermined curves developed and stored in advance.

14. A method for sensing vapor, comprising steps of:
exposing a porous optical film to vapor which contains analyte;
heating the porous optical film;
monitoring an optical response of the porous optical film for a sensing time period during said heating; and
determining identity or quantity of the analyte from a response curve obtained during the sensing time period of said monitoring, wherein the porous optical film comprises a Rugate filter.

15. A method for sensing vapor, comprising steps of:
exposing a porous optical film to vapor which contains analyte;
heating the porous optical film;
monitoring an optical response of the porous optical film for a sensing time period during said heating; and
determining identity or quantity of the analyte from a response curve obtained during the sensing time period of said monitoring, wherein said porous optical film comprises carbonized silicon.

16. The method of claim 15, wherein the porous optical film comprises a Rugate filter.

17. A method for sensing vapor, comprising steps of:
exposing a porous optical film to a vapor which contains analyte;
heating the porous optical film;
monitoring on optical response of the porous optical film for a sensing time period during said heating for a shift in spectral position of an optical band gap during said exposing and heating;
ceasing said heating after a heating time period to cycle the porous optical film over a heating cycle and cooling cycle, wherein said monitoring encompasses at least a portion of said heating cycle and said cooling cycle;
identifying analyte in the vapor by comparing an observed shift in spectral position of the optical bandgap with a database of previously determined analyte specific shifts in spectral positions.

18. The method of claim 17, further comprising quantifying analyte identified by said step of identifying.

19. The method of claim 17, further comprising a step of changing the vapor pressure during said monitoring.

20. A system for sensing analyte in vapor, the system comprising:
a porous optical film;
a heater for heating the porous optical film;
an optical sensor for sensing optical response of the optical film; and
controllers and nontransient computer readable medium for storing code that performs the method of claim 17.

21. A method for sensing vapor, comprising steps of:
adsorbing analyte into a porous optical film;
heating the porous optical film; and
monitoring on optical response of the porous optical film for a sensing time period during said heating for a shift in spectral position of an optical band gap during said adsorbing and heating;
wherein said heating comprises heating to a desorption temperature and the sensing time period covers a period of desorption; and
identifying analyte adsorbed into the porous optical film through one of changes in the wavelength position of the optical film's spectral peak(s), and rate of change, shape, or functional form of the sensor optical response.

22. The method of claim 21, wherein said identifying comprises comparing an observed shift in spectral position of the optical bandgap with a database of previously determined analyte specific shifts in spectral positions.

23. The method of claim 22, further comprising a step of changing the vapor pressure during said monitoring.

* * * * *